(12) United States Patent
Schmitt et al.

(10) Patent No.: US 9,034,604 B2
(45) Date of Patent: May 19, 2015

(54) COMPOSITION COMPRISING AN OLIGONUCLEOTIDE MIXTURE FOR THE DETECTION OF CONTAMINATIONS IN CELL CULTURES

(75) Inventors: Markus Schmitt, Heidelberg (DE); Michael Pawlita, Eschelbronn (DE)

(73) Assignee: DKFZ Deutsches Krebsforschungszentrum, Heidelberg (DE)

( * ) Notice: Subject to any disclaimer, the term of this patent is extended or adjusted under 35 U.S.C. 154(b) by 768 days.

(21) Appl. No.: 12/920,095

(22) PCT Filed: Mar. 5, 2009

(86) PCT No.: PCT/EP2009/052575
§ 371 (c)(1),
(2), (4) Date: Nov. 22, 2010

(87) PCT Pub. No.: WO2009/109611
PCT Pub. Date: Sep. 11, 2009

(65) Prior Publication Data
US 2011/0091885 A1    Apr. 21, 2011

(30) Foreign Application Priority Data
Mar. 5, 2008   (EP) .................................... 08152321

(51) Int. Cl.
*C12Q 1/68*   (2006.01)
*C12Q 1/70*   (2006.01)

(52) U.S. Cl.
CPC .............. *C12Q 1/689* (2013.01); *C12Q 1/6881* (2013.01); *C12Q 1/701* (2013.01); *C12Q 1/702* (2013.01); *C12Q 1/705* (2013.01); *C12Q 1/686* (2013.01)

(58) Field of Classification Search
None
See application file for complete search history.

(56) References Cited

U.S. PATENT DOCUMENTS 6,815,161 B1   11/2004   Vojdani
2003/0108864 A1   6/2003   Liu et al.

OTHER PUBLICATIONS

Sun et al. (1995) Virology 209 (2), 374-383.*
Oda et al. (1988) Virology vol. 167 (2) 468-476.*
Yoshida et al. (2002) J. Clinical Microbiol. vol. 40 No. 1 pp. 105-110.*
Kinniburgh et al. (1982) Nucl. Acids Res. vol. 10. No. 18; pp. 5421-5427.*
Birke et al. (1981) The j. of immunology vol. 127 No. 1 94-98 ( abstract provided).*
Liu et al. (2001) J. Clin Microbiol. vol. 39(5):1941-1946.*
Paunesku et al. (1990) Mol. Biol. Evol. 7 (5), 407-422.*
Roberts (online publication date Sep. 6, 2007) chapter 19 Virus Safety of cell derived biological products pp. 371-392 in Medicines from Animal Cell Culture edited by G. Stacey and J. Davis (published by John Wiley & Sons, Ltd.).*
Higgins et al., "Fast and Sensitive Multiple Sequence Alignments on a Microcomputer," *CABIOS Communications*, vol. 5, No. 2, pp. 151-153 (1989).
Feng et al., "Progressive Sequence Alignment as a Prerequisite to Correct Phylogenetic Trees," *J. Mol. Evol.*, vol. 25, pp. 351-360 (1987).
Needleman et al., "A General Method Applicable to the Search for Similarities in the Amino Acid Sequence of Two Proteins," *J. Mol. Biol.*, vol. 48, pp. 443-453 (1970).
Smith et al., "Comparison of Biosequences," *Advances in Applied Mathematics*, vol. 2, pp. 482-489 (1981).
Uphoff et al., "Comparative PCR Analysis for Detection of Mycoplasma Infections in Continuous Cell Lines," *In Vitro Cell. Dev. Biol.-Animal*, vol. 38, pp. 79-85 (2002).
Tang et al.: "Primor Mixture Enhances PCR Detection of Mycoplasma/Acholeplasma Contaminents in Cell Cultures", *In Vitro Cellular & Developmental Biology*, Animal, vol. 35, No. 1, pp. 1-3 (1999).
Cooper, et al., "Species Indentification in Cell Culture: a two-pronged molecular approach." *In Vitro Cellular & Developmental Biology*, Animal 2007, vol. 43, No. 10, pp. 344-351 (2007).
Cobo et al., "Microbiological Contamination in Stem Cell Cultures", *Cell Biology International*, vol. 31, No. 9, pp. 991-995 (2007).
Lam et al., "Rapid Multiplex Nested PCR for Detection of Respiratiory Viruses." *Journal of Clinical Microbiology*, vol. 45, No. 11, pp. 3631-3640. (2007).
Middleton et al., "Insertion of SMRV-H 1-15 Viral DNA at the C-MYC Gene Locus of a BL Cell Line and Presence in Established Cell Lines", *International Journal of Cancer*, vol. 52, pp. 451-454 (1992).
International Preliminary Report on Patentability for related International Patent Application No. PCT/EP2009/052575, completed Jun. 16, 2010.
International Search Report for related International Patent Application No. PCT/EP2009/052575, mailed Jun. 18, 2009.
Written Opinion for related International Patent Application No. PCT/EP2009/052575, mailed Jun. 18, 2009.

* cited by examiner

*Primary Examiner* — Suchira Pande
(74) *Attorney, Agent, or Firm* — Foley & Lardner LLP

(57) ABSTRACT

The present invention relates to a method for determining contaminations in a cell culture sample comprising the steps of: a) contacting a sample of a cell culture suspected to comprise contaminations with a composition comprising oligonucleotides under conditions which allow for amplification of polynucleotides, wherein said oligonucleotides comprise oligonucleotides of at least three different groups of oligonucleotides, and b) determining the contaminations based on the amplified polynucleotides obtained by using the oligonucleotide groups of step (a). Moreover, the invention relates to a composition comprising an oligonucleotide mixture. Further encompassed by the present invention is a composition comprising a probe oligonucleotide mixture. Finally, the present invention also relates to kits comprising said oligonucleotide mixtures.

7 Claims, No Drawings

SEQUENCE LISTING

<160> NUMBER OF SEQ ID NOS: 165

<210> SEQ ID NO 1
<211> LENGTH: 24
<212> TYPE: DNA
<213> ORGANISM: artificial
<220> FEATURE:
<223> OTHER INFORMATION: primer Smrv_gag_f

<400> SEQUENCE: 1
tcagagccca ccgagcctac ctac                                              24

<210> SEQ ID NO 2
<211> LENGTH: 23
<212> TYPE: DNA
<213> ORGANISM: artificial
<220> FEATURE:
<223> OTHER INFORMATION: primer Smrv_gag_b

<400> SEQUENCE: 2
cagcgcagca cgagacaaga aaa                                               23

<210> SEQ ID NO 3
<211> LENGTH: 21
<212> TYPE: DNA
<213> ORGANISM: artificial
<220> FEATURE:
<223> OTHER INFORMATION: primer Smrv_env_f

<400> SEQUENCE: 3
ggcggacccc aagatgctgt g                                                 21

<210> SEQ ID NO 4
<211> LENGTH: 24
<212> TYPE: DNA
<213> ORGANISM: artificial
<220> FEATURE:
<223> OTHER INFORMATION: primer Smrv_env_b

<400> SEQUENCE: 4
tgggctaggc tggggttgga gata                                              24

<210> SEQ ID NO 5
<211> LENGTH: 25
<212> TYPE: DNA
<213> ORGANISM: artificial
<220> FEATURE:
<223> OTHER INFORMATION: primer Myco_fl

<400> SEQUENCE: 5
tggggagcaa ataggattag atacc                                             25

<210> SEQ ID NO 6
<211> LENGTH: 25
<212> TYPE: DNA
<213> ORGANISM: artificial
<220> FEATURE:
<223> OTHER INFORMATION: primer Myco_bl

<400> SEQUENCE: 6
gtaccgtcga attaagcaac atgct                                             25

<210> SEQ ID NO 7
<211> LENGTH: 25
<212> TYPE: DNA
<213> ORGANISM: artificial

```
<220> FEATURE:
<223> OTHER INFORMATION: primer Myco_f2

<400> SEQUENCE: 7
tggggagcaa acaggattag atacc                                          25

<210> SEQ ID NO 8
<211> LENGTH: 25
<212> TYPE: DNA
<213> ORGANISM: artificial
<220> FEATURE:
<223> OTHER INFORMATION: primer Myco_b2

<400> SEQUENCE: 8
tatcttcaaa ttaaaccaca tgctc                                          25

<210> SEQ ID NO 9
<211> LENGTH: 24
<212> TYPE: DNA
<213> ORGANISM: artificial
<220> FEATURE:
<223> OTHER INFORMATION: primer HPV_18_f

<400> SEQUENCE: 9
gaccttctat gtcacgagca atta                                           24

<210> SEQ ID NO 10
<211> LENGTH: 22
<212> TYPE: DNA
<213> ORGANISM: artificial
<220> FEATURE:
<223> OTHER INFORMATION: primer HPV_18_b

<400> SEQUENCE: 10
tgcacaccac ggacacacaa ag                                             22

<210> SEQ ID NO 11
<211> LENGTH: 23
<212> TYPE: DNA
<213> ORGANISM: artificial
<220> FEATURE:
<223> OTHER INFORMATION: primer Adeno-f

<400> SEQUENCE: 11
gtgtctgaac ctgagcctga gcc                                            23

<210> SEQ ID NO 12
<211> LENGTH: 24
<212> TYPE: DNA
<213> ORGANISM: artificial
<220> FEATURE:
<223> OTHER INFORMATION: primer Adeno_b

<400> SEQUENCE: 12
gaggtgtgtt agaaggaccg gagt                                           24

<210> SEQ ID NO 13
<211> LENGTH: 24
<212> TYPE: DNA
<213> ORGANISM: artificial
<220> FEATURE:
<223> OTHER INFORMATION: primer Acholeplasma_f

<400> SEQUENCE: 13
ggggatggat cacctccttt ctaa                                           24
```

```
<210> SEQ ID NO 14
<211> LENGTH: 24
<212> TYPE: DNA
<213> ORGANISM: artificial
<220> FEATURE:
<223> OTHER INFORMATION: primer Acholeplasma_b

<400> SEQUENCE: 14
caagcgagtg ctctaaccaa ctga                                              24

<210> SEQ ID NO 15
<211> LENGTH: 26
<212> TYPE: DNA
<213> ORGANISM: artificial
<220> FEATURE:
<223> OTHER INFORMATION: primer Bg_human/monkey_f

<400> SEQUENCE: 15
tgaccaaatc agggtaattt tgcatt                                            26

<210> SEQ ID NO 16
<211> LENGTH: 26
<212> TYPE: DNA
<213> ORGANISM: artificial
<220> FEATURE:
<223> OTHER INFORMATION: primer Bg_human/monkey_b

<400> SEQUENCE: 16
agaatggtgc aaagaggcat gataca                                            26

<210> SEQ ID NO 17
<211> LENGTH: 25
<212> TYPE: DNA
<213> ORGANISM: artificial
<220> FEATURE:
<223> OTHER INFORMATION: Primer Bg_mouse_f

<400> SEQUENCE: 17
gctgagacgt cctaagccag tgagt                                             25

<210> SEQ ID NO 18
<211> LENGTH: 26
<212> TYPE: DNA
<213> ORGANISM: artificial
<220> FEATURE:
<223> OTHER INFORMATION: primer Bg_mouse_b

<400> SEQUENCE: 18
tctggggttg tgagtcaaca caacta                                            26

<210> SEQ ID NO 19
<211> LENGTH: 24
<212> TYPE: DNA
<213> ORGANISM: artificial
<220> FEATURE:
<223> OTHER INFORMATION: primer Bg_rat_f

<400> SEQUENCE: 19
agcctgtacc atagccaccc tgag                                              24

<210> SEQ ID NO 20
<211> LENGTH: 26
<212> TYPE: DNA
<213> ORGANISM: artificial
<220> FEATURE:
<223> OTHER INFORMATION: primer Bg_rat_b
```

```
<400> SEQUENCE: 20
cctgaggttg cgagtcaaca caacag                                         26

<210> SEQ ID NO 21
<211> LENGTH: 25
<212> TYPE: DNA
<213> ORGANISM: artificial
<220> FEATURE:
<223> OTHER INFORMATION: primer HBV_f

<400> SEQUENCE: 21
ggtggacttc tctcaatttt ctagg                                          25

<210> SEQ ID NO 22
<211> LENGTH: 24
<212> TYPE: DNA
<213> ORGANISM: artificial
<220> FEATURE:
<223> OTHER INFORMATION: primer HBV_b

<400> SEQUENCE: 22
atgataaaac gccgcagaca catc                                           24

<210> SEQ ID NO 23
<211> LENGTH: 23
<212> TYPE: DNA
<213> ORGANISM: artificial
<220> FEATURE:
<223> OTHER INFORMATION: primer HSV1_f

<400> SEQUENCE: 23
acgaggccgc agctcaccaa ggt                                            23

<210> SEQ ID NO 24
<211> LENGTH: 22
<212> TYPE: DNA
<213> ORGANISM: artificial
<220> FEATURE:
<223> OTHER INFORMATION: primer HSV1_b

<400> SEQUENCE: 24
cgccctcctc gcgggcagca aa                                             22

<210> SEQ ID NO 25
<211> LENGTH: 23
<212> TYPE: DNA
<213> ORGANISM: artificial
<220> FEATURE:
<223> OTHER INFORMATION: primer HSV2_f

<400> SEQUENCE: 25
acgaagcccc agctcacgaa ggt                                            23

<210> SEQ ID NO 26
<211> LENGTH: 22
<212> TYPE: DNA
<213> ORGANISM: artificial
<220> FEATURE:
<223> OTHER INFORMATION: primer HSV2_b

<400> SEQUENCE: 26
cgccctcctc gcgggcggca aa                                             22

<210> SEQ ID NO 27
```

```
<211> LENGTH: 24
<212> TYPE: DNA
<213> ORGANISM: artificial
<220> FEATURE:
<223> OTHER INFORMATION: primer VZV_f

<400> SEQUENCE: 27
catccttcac agattccatg ttcg                                              24

<210> SEQ ID NO 28
<211> LENGTH: 24
<212> TYPE: DNA
<213> ORGANISM: artificial
<220> FEATURE:
<223> OTHER INFORMATION: primer VZV_b

<400> SEQUENCE: 28
tcccccatgg ttggattgta tatc                                              24

<210> SEQ ID NO 29
<211> LENGTH: 24
<212> TYPE: DNA
<213> ORGANISM: artificial
<220> FEATURE:
<223> OTHER INFORMATION: primer EBV_f

<400> SEQUENCE: 29
ttatttaacc acgcctccga agag                                              24

<210> SEQ ID NO 30
<211> LENGTH: 24
<212> TYPE: DNA
<213> ORGANISM: artificial
<220> FEATURE:
<223> OTHER INFORMATION: primer EBV_b

<400> SEQUENCE: 30
tgaaggagat ggactgaccg tatg                                              24

<210> SEQ ID NO 31
<211> LENGTH: 24
<212> TYPE: DNA
<213> ORGANISM: artificial
<220> FEATURE:
<223> OTHER INFORMATION: primer CMV_f

<400> SEQUENCE: 31
gttcccgacg taattttgt cgaa                                               24

<210> SEQ ID NO 32
<211> LENGTH: 24
<212> TYPE: DNA
<213> ORGANISM: artificial
<220> FEATURE:
<223> OTHER INFORMATION: primer CMV_b

<400> SEQUENCE: 32
gcacgttgcg tatagttacg gagc                                              24

<210> SEQ ID NO 33
<211> LENGTH: 24
<212> TYPE: DNA
<213> ORGANISM: artificial
<220> FEATURE:
<223> OTHER INFORMATION: primer HHV6_f

<400> SEQUENCE: 33
```
aaataagcta gagcccgcag ttcc                                          24

<210> SEQ ID NO 34
<211> LENGTH: 24
<212> TYPE: DNA
<213> ORGANISM: artificial
<220> FEATURE:
<223> OTHER INFORMATION: primer HHV6_b

<400> SEQUENCE: 34
acgaatgggt aaacaagatg acgg                                          24

<210> SEQ ID NO 35
<211> LENGTH: 24
<212> TYPE: DNA
<213> ORGANISM: artificial
<220> FEATURE:
<223> OTHER INFORMATION: primer HHV7_f

<400> SEQUENCE: 35
tgaaacacaa ctttcccgct atga                                          24

<210> SEQ ID NO 36
<211> LENGTH: 24
<212> TYPE: DNA
<213> ORGANISM: artificial
<220> FEATURE:
<223> OTHER INFORMATION: primer HHV7_b

<400> SEQUENCE: 36
cggtcacaaa gaacaaacgc agta                                          24

<210> SEQ ID NO 37
<211> LENGTH: 24
<212> TYPE: DNA
<213> ORGANISM: artificial
<220> FEATURE:
<223> OTHER INFORMATION: primer HHV8_f

<400> SEQUENCE: 37
gacttcttcc ccttcagacc atcc                                          24

<210> SEQ ID NO 38
<211> LENGTH: 24
<212> TYPE: DNA
<213> ORGANISM: artificial
<220> FEATURE:
<223> OTHER INFORMATION: primer HHV8_b

<400> SEQUENCE: 38
aaacaaaaga ggaccaaacg gtga                                          24

<210> SEQ ID NO 39
<211> LENGTH: 24
<212> TYPE: DNA
<213> ORGANISM: artificial
<220> FEATURE:
<223> OTHER INFORMATION: primer Y_hum/mon_f

<400> SEQUENCE: 39
gtacgaaagc cacacactca agaa                                          24

<210> SEQ ID NO 40
<211> LENGTH: 24
<212> TYPE: DNA

```
<213> ORGANISM: artificial
<220> FEATURE:
<223> OTHER INFORMATION: primer Y_hum/mon_b

<400> SEQUENCE: 40
ttgtcctaca gctttgtcca gtgg                                              24

<210> SEQ ID NO 41
<211> LENGTH: 25
<212> TYPE: DNA
<213> ORGANISM: artificial
<220> FEATURE:
<223> OTHER INFORMATION: primer Y_rat_f

<400> SEQUENCE: 41
ggaggagacc aaaatgtgtg taagg                                             25

<210> SEQ ID NO 42
<211> LENGTH: 25
<212> TYPE: DNA
<213> ORGANISM: artificial
<220> FEATURE:
<223> OTHER INFORMATION: primer Y_rat_b

<400> SEQUENCE: 42
catcgattaa atgccataag aatgc                                             25

<210> SEQ ID NO 43
<211> LENGTH: 25
<212> TYPE: DNA
<213> ORGANISM: artificial
<220> FEATURE:
<223> OTHER INFORMATION: primer Y_mouse_f

<400> SEQUENCE: 43
tccatgacca ccaccagcag aagca                                             25

<210> SEQ ID NO 44
<211> LENGTH: 23
<212> TYPE: DNA
<213> ORGANISM: artificial
<220> FEATURE:
<223> OTHER INFORMATION: primer Y_mouse_b

<400> SEQUENCE: 44
ctgggggtgg tcatggaact gat                                               23

<210> SEQ ID NO 45
<211> LENGTH: 25
<212> TYPE: DNA
<213> ORGANISM: artificial
<220> FEATURE:
<223> OTHER INFORMATION: primer SV40 VP1_f

<400> SEQUENCE: 45
gaacctacac aggtggggaa aatgt                                             25

<210> SEQ ID NO 46
<211> LENGTH: 23
<212> TYPE: DNA
<213> ORGANISM: artificial
<220> FEATURE:
<223> OTHER INFORMATION: primer SV40 VP1_b

<400> SEQUENCE: 46
caagggccca acaccctgct cat                                               23
```

```
<210> SEQ ID NO 47
<211> LENGTH: 25
<212> TYPE: DNA
<213> ORGANISM: artificial
<220> FEATURE:
<223> OTHER INFORMATION: primer SV40 Tag_f

<400> SEQUENCE: 47 aacctgttttt gctcagaaga aatgc                                          25

<210> SEQ ID NO 48
<211> LENGTH: 25
<212> TYPE: DNA
<213> ORGANISM: artificial
<220> FEATURE:
<223> OTHER INFORMATION: primer SV40 Tag_b

<400> SEQUENCE: 48
gaaggaaagt ccttggggtc ttcta                                           25

<210> SEQ ID NO 49
<211> LENGTH: 24
<212> TYPE: DNA
<213> ORGANISM: artificial
<220> FEATURE:
<223> OTHER INFORMATION: primer SV40 VP3_f_bio

<400> SEQUENCE: 49
aagcttatga agatggcccc aaca                                            24

<210> SEQ ID NO 50
<211> LENGTH: 25
<212> TYPE: DNA
<213> ORGANISM: artificial
<220> FEATURE:
<223> OTHER INFORMATION: primer SV40 VP3_b

<400> SEQUENCE: 50
attcctcctt ttatgacgag ctttg                                           25

<210> SEQ ID NO 51
<211> LENGTH: 26
<212> TYPE: DNA
<213> ORGANISM: artificial
<220> FEATURE:
<223> OTHER INFORMATION: primer POLA_f

<400> SEQUENCE: 51
tcagaaatag ttcttgatcg ggtttg                                          26

<210> SEQ ID NO 52
<211> LENGTH: 25
<212> TYPE: DNA
<213> ORGANISM: artificial
<220> FEATURE:
<223> OTHER INFORMATION: primer POLA_b

<400> SEQUENCE: 52
taaatgcagc tgcctctttc aatgc                                           25

<210> SEQ ID NO 53
<211> LENGTH: 23
<212> TYPE: DNA
<213> ORGANISM: artificial
<220> FEATURE:
```

```
<223> OTHER INFORMATION: primer CH_f

<400> SEQUENCE: 53
ccgaatgatt atagctaagg cac                                              23

<210> SEQ ID NO 54
<211> LENGTH: 23
<212> TYPE: DNA
<213> ORGANISM: artificial
<220> FEATURE:
<223> OTHER INFORMATION: primer CH_b

<400> SEQUENCE: 54
cttggtccgt tgatcaaata tgt                                              23

<210> SEQ ID NO 55
<211> LENGTH: 23
<212> TYPE: DNA
<213> ORGANISM: artificial
<220> FEATURE:
<223> OTHER INFORMATION: primer Dog_f

<400> SEQUENCE: 55
ccgagtgatt aaaatttaga ccc                                              23

<210> SEQ ID NO 56
<211> LENGTH: 23
<212> TYPE: DNA
<213> ORGANISM: artificial
<220> FEATURE:
<223> OTHER INFORMATION: primer Dog_b

<400> SEQUENCE: 56
ttgttccgtt gatcaaaaat tat                                              23

<210> SEQ ID NO 57
<211> LENGTH: 23
<212> TYPE: DNA
<213> ORGANISM: artificial
<220> FEATURE:
<223> OTHER INFORMATION: primer Cat_f

<400> SEQUENCE: 57
ccgagtgatt taaatctaga cta                                              23

<210> SEQ ID NO 58
<211> LENGTH: 23
<212> TYPE: DNA
<213> ORGANISM: artificial
<220> FEATURE:
<223> OTHER INFORMATION: primer Cat_b

<400> SEQUENCE: 58
cttgttccgt tgatcaaggt ttt                                              23

<210> SEQ ID NO 59
<211> LENGTH: 23
<212> TYPE: DNA
<213> ORGANISM: artificial
<220> FEATURE:
<223> OTHER INFORMATION: primer Gree_mo_f

<400> SEQUENCE: 59
cgaacaatcc atgctaagac tac                                              23
```

<210> SEQ ID NO 60
<211> LENGTH: 24
<212> TYPE: DNA
<213> ORGANISM: artificial
<220> FEATURE:
<223> OTHER INFORMATION: primer Gree_mo_b

<400> SEQUENCE: 60
acttgttcca ttgatcaaat tatt                                    24

<210> SEQ ID NO 61
<211> LENGTH: 23
<212> TYPE: DNA
<213> ORGANISM: artificial
<220> FEATURE:
<223> OTHER INFORMATION: primer mouse_f

<400> SEQUENCE: 61
ccgaatgatt ataacctaga ctt                                     23

<210> SEQ ID NO 62
<211> LENGTH: 23
<212> TYPE: DNA
<213> ORGANISM: artificial
<220> FEATURE:
<223> OTHER INFORMATION: primer mouse_b

<400> SEQUENCE: 62
tggtccgttg atcaaaatat atc                                     23

<210> SEQ ID NO 63
<211> LENGTH: 24
<212> TYPE: DNA
<213> ORGANISM: artificial
<220> FEATURE:
<223> OTHER INFORMATION: primer Rat_f

<400> SEQUENCE: 63
aataaacaac tacaatcact taac                                    24

<210> SEQ ID NO 64
<211> LENGTH: 24
<212> TYPE: DNA
<213> ORGANISM: artificial
<220> FEATURE:
<223> OTHER INFORMATION: primer Rat_b

<400> SEQUENCE: 64
tatagattag cccaatttgt gata                                    24

<210> SEQ ID NO 65
<211> LENGTH: 23
<212> TYPE: DNA
<213> ORGANISM: artificial
<220> FEATURE:
<223> OTHER INFORMATION: primer Cyno_f

<400> SEQUENCE: 65
cgaataacac atgccaagac tac                                     23

<210> SEQ ID NO 66
<211> LENGTH: 24
<212> TYPE: DNA
<213> ORGANISM: artificial
<220> FEATURE:
<223> OTHER INFORMATION: primer Cyno_b

<400> SEQUENCE: 66
acttgttccg ttgatcaaat aatt                                    24

<210> SEQ ID NO 67
<211> LENGTH: 26
<212> TYPE: DNA
<213> ORGANISM: artificial
<220> FEATURE:
<223> OTHER INFORMATION: primer HIV1_gag_f

<400> SEQUENCE: 67
ggaagtgaya tagcwggaac tacyag                                  26

<210> SEQ ID NO 68
<211> LENGTH: 23
<212> TYPE: DNA
<213> ORGANISM: artificial
<220> FEATURE:
<223> OTHER INFORMATION: primer HIV1_gag_b

<400> SEQUENCE: 68
acagggctat acattcttac tat                                     23

<210> SEQ ID NO 69
<211> LENGTH: 24
<212> TYPE: DNA
<213> ORGANISM: artificial
<220> FEATURE:
<223> OTHER INFORMATION: primer HIV1_M,O_pol_f

<400> SEQUENCE: 69
atagtracag aytcacarta tgca                                    24

<210> SEQ ID NO 70
<211> LENGTH: 24
<212> TYPE: DNA
<213> ORGANISM: artificial
<220> FEATURE:
<223> OTHER INFORMATION: primer HIV1_N_pol_f

<400> SEQUENCE: 70
atagtcactg actctcagta tgct                                    24

<210> SEQ ID NO 71
<211> LENGTH: 25
<212> TYPE: DNA
<213> ORGANISM: artificial
<220> FEATURE:
<223> OTHER INFORMATION: primer HIV1_M,N,O_pol_b

<400> SEQUENCE: 71
atttatctac ttgttcattt cctcc                                   25

<210> SEQ ID NO 72
<211> LENGTH: 23
<212> TYPE: DNA
<213> ORGANISM: artificial
<220> FEATURE:
<223> OTHER INFORMATION: primer HIV1_O/N_gag_f-bio

<400> SEQUENCE: 72
gggattgggg ggtacactgc agg                                     23

<210> SEQ ID NO 73
<211> LENGTH: 25

```
<212> TYPE: DNA
<213> ORGANISM: artificial
<220> FEATURE:
<223> OTHER INFORMATION: primer HIV1_O/N_gag_b

<400> SEQUENCE: 73
ctgctgtctc tgtaatarac ccgaa                                          25

<210> SEQ ID NO 74
<211> LENGTH: 25
<212> TYPE: DNA
<213> ORGANISM: artificial
<220> FEATURE:
<223> OTHER INFORMATION: primer HIV2/SIV_pol_f

<400> SEQUENCE: 74 gaagggagg aatagggat atgac                                            25

<210> SEQ ID NO 75
<211> LENGTH: 24
<212> TYPE: DNA
<213> ORGANISM: artificial
<220> FEATURE:
<223> OTHER INFORMATION: primer HIV2/SIV_pol_b

<400> SEQUENCE: 75
tctgccttct ctgwaataga cccg                                           24

<210> SEQ ID NO 76
<211> LENGTH: 27
<212> TYPE: DNA
<213> ORGANISM: artificial
<220> FEATURE:
<223> OTHER INFORMATION: primer HIV2/SIV_env_f

<400> SEQUENCE: 76
acgttgtcgg ctcagtcycg gacttta                                        27

<210> SEQ ID NO 77
<211> LENGTH: 25
<212> TYPE: DNA
<213> ORGANISM: artificial
<220> FEATURE:
<223> OTHER INFORMATION: primer HIV2/SIV_env_b

<400> SEQUENCE: 77
gtcccccaga cggtcagycg caaca                                          25

<210> SEQ ID NO 78
<211> LENGTH: 20
<212> TYPE: DNA
<213> ORGANISM: artificial
<220> FEATURE:
<223> OTHER INFORMATION: probe M. orale

<400> SEQUENCE: 78
tcggtggaaa actactgacg                                                20

<210> SEQ ID NO 79
<211> LENGTH: 20
<212> TYPE: DNA
<213> ORGANISM: artificial
<220> FEATURE:
<223> OTHER INFORMATION: probe M. hyorhinis

<400> SEQUENCE: 79
```
ggaataattt cactaacgca                                              20

<210> SEQ ID NO 80
<211> LENGTH: 20
<212> TYPE: DNA
<213> ORGANISM: artificial
<220> FEATURE:
<223> OTHER INFORMATION: probe M. arginini

<400> SEQUENCE: 80
gtggagagtt cactgacgca                                              20

<210> SEQ ID NO 81
<211> LENGTH: 20
<212> TYPE: DNA
<213> ORGANISM: artificial
<220> FEATURE:
<223> OTHER INFORMATION: probe M. fermentans

<400> SEQUENCE: 81
ctgatgggga actcatcggc                                              20

<210> SEQ ID NO 82
<211> LENGTH: 20
<212> TYPE: DNA
<213> ORGANISM: artificial
<220> FEATURE:
<223> OTHER INFORMATION: probe M. salivarium

<400> SEQUENCE: 82
tcggcagaga actgttgacg                                              20

<210> SEQ ID NO 83
<211> LENGTH: 20
<212> TYPE: DNA
<213> ORGANISM: artificial
<220> FEATURE:
<223> OTHER INFORMATION: probe M. hominis

<400> SEQUENCE: 83
cggtggagaa tcactgacgc                                              20

<210> SEQ ID NO 84
<211> LENGTH: 20
<212> TYPE: DNA
<213> ORGANISM: artificial
<220> FEATURE:
<223> OTHER INFORMATION: probe M. synoviae

<400> SEQUENCE: 84
ttgatagaaa ccatcgacgc                                              20

<210> SEQ ID NO 85
<211> LENGTH: 19
<212> TYPE: DNA
<213> ORGANISM: artificial
<220> FEATURE:
<223> OTHER INFORMATION: probe M. gallisepticum

<400> SEQUENCE: 85
tgtcggagcg aatacttcg                                               19

<210> SEQ ID NO 86
<211> LENGTH: 19
<212> TYPE: DNA
<213> ORGANISM: artificial

<220> FEATURE:
<223> OTHER INFORMATION: probe Myo-uni 1

<400> SEQUENCE: 86
gatccgcctg agtagtatg                                          19

<210> SEQ ID NO 87
<211> LENGTH: 20
<212> TYPE: DNA
<213> ORGANISM: artificial
<220> FEATURE:
<223> OTHER INFORMATION: probe M. pneumoniae

<400> SEQUENCE: 87
ggcgatcccc tcggtagtga                                         20

<210> SEQ ID NO 88
<211> LENGTH: 20
<212> TYPE: DNA
<213> ORGANISM: artificial
<220> FEATURE:
<223> OTHER INFORMATION: probe M. pirum

<400> SEQUENCE: 88
ggtaaacgcc tcggtgtcgt                                         20

<210> SEQ ID NO 89
<211> LENGTH: 22
<212> TYPE: DNA
<213> ORGANISM: artificial
<220> FEATURE:
<223> OTHER INFORMATION: probe Myco-uni 2

<400> SEQUENCE: 89
tacattcgca agaatgaaac tt                                      22

<210> SEQ ID NO 90
<211> LENGTH: 21
<212> TYPE: DNA
<213> ORGANISM: artificial
<220> FEATURE:
<223> OTHER INFORMATION: probe A. laidlawii

<400> SEQUENCE: 90
actcaaacaa gtaaccacat a                                       21

<210> SEQ ID NO 91
<211> LENGTH: 20
<212> TYPE: DNA
<213> ORGANISM: artificial
<220> FEATURE:
<223> OTHER INFORMATION: probe A. granularum

<400> SEQUENCE: 91
gtacactcaa acctcataat                                         20

<210> SEQ ID NO 92
<211> LENGTH: 18
<212> TYPE: DNA
<213> ORGANISM: artificial
<220> FEATURE:
<223> OTHER INFORMATION: probe HPV18

<400> SEQUENCE: 92
cagacgacct tcgagcat                                           18

<210> SEQ ID NO 93
<211> LENGTH: 20
<212> TYPE: DNA
<213> ORGANISM: artificial
<220> FEATURE:
<223> OTHER INFORMATION: probe Rat beta globin

<400> SEQUENCE: 93
atataaagca gaacagaacc                                                  20

<210> SEQ ID NO 94
<211> LENGTH: 20
<212> TYPE: DNA
<213> ORGANISM: artificial
<220> FEATURE:
<223> OTHER INFORMATION: probe mouse beta globin

<400> SEQUENCE: 94
atataaggtg aggtaggatc                                                  20

<210> SEQ ID NO 95
<211> LENGTH: 18
<212> TYPE: DNA
<213> ORGANISM: artificial
<220> FEATURE:
<223> OTHER INFORMATION: probe cynomolgus beta globin

<400> SEQUENCE: 95
caaggcaata accataca                                                    18

<210> SEQ ID NO 96
<211> LENGTH: 18
<212> TYPE: DNA
<213> ORGANISM: artificial
<220> FEATURE:
<223> OTHER INFORMATION: probe human beta globin

<400> SEQUENCE: 96
cagggcaata atgataca                                                    18

<210> SEQ ID NO 97
<211> LENGTH: 21
<212> TYPE: DNA
<213> ORGANISM: artificial
<220> FEATURE:
<223> OTHER INFORMATION: probe Human/monkey beta globin

<400> SEQUENCE: 97
ctaatacttt ccctaatctc t                                                21

<210> SEQ ID NO 98
<211> LENGTH: 22
<212> TYPE: DNA
<213> ORGANISM: artificial
<220> FEATURE:
<223> OTHER INFORMATION: probe Mammal IC

<400> SEQUENCE: 98
gtacatctga ttactgaagt ac                                               22

<210> SEQ ID NO 99
<211> LENGTH: 19
<212> TYPE: DNA
<213> ORGANISM: artificial
<220> FEATURE:
<223> OTHER INFORMATION: probe Adenovirus 1,2

```
<400> SEQUENCE: 99
tcctaaattg gtgcctgct                                              19

<210> SEQ ID NO 100
<211> LENGTH: 19
<212> TYPE: DNA
<213> ORGANISM: artificial
<220> FEATURE:
<223> OTHER INFORMATION: probe Adenovirus 5

<400> SEQUENCE: 100
gccgtcctaa aatggcgcc                                              19

<210> SEQ ID NO 101
<211> LENGTH: 17
<212> TYPE: DNA
<213> ORGANISM: artificial
<220> FEATURE:
<223> OTHER INFORMATION: probe Adenovirus 6

<400> SEQUENCE: 101
cctgtgtcca gagaatg                                                17

<210> SEQ ID NO 102
<211> LENGTH: 20
<212> TYPE: DNA
<213> ORGANISM: artificial
<220> FEATURE:
<223> OTHER INFORMATION: probe Adenovirus 1,2,5,6

<400> SEQUENCE: 102
gcaatagtag tacggatagc                                             20

<210> SEQ ID NO 103
<211> LENGTH: 25
<212> TYPE: DNA
<213> ORGANISM: artificial
<220> FEATURE:
<223> OTHER INFORMATION: probe SMRV

<400> SEQUENCE: 103
ggcccttgta gagagtctta gtgaa                                       25

<210> SEQ ID NO 104
<211> LENGTH: 25
<212> TYPE: DNA
<213> ORGANISM: artificial
<220> FEATURE:
<223> OTHER INFORMATION: probe SMRV_env

<400> SEQUENCE: 104
tgcttgatat tctgtcagcc accca                                       25

<210> SEQ ID NO 105
<211> LENGTH: 18
<212> TYPE: DNA
<213> ORGANISM: artificial
<220> FEATURE:
<223> OTHER INFORMATION: probe HBV A

<400> SEQUENCE: 105
ttgtcctggt tatcgctg                                               18

<210> SEQ ID NO 106
```

```
<211> LENGTH: 19
<212> TYPE: DNA
<213> ORGANISM: artificial
<220> FEATURE:
<223> OTHER INFORMATION: probe HBV A

<400> SEQUENCE: 106
gtcctccaat tgtcctgg                                                  19

<210> SEQ ID NO 107
<211> LENGTH: 18
<212> TYPE: DNA
<213> ORGANISM: artificial
<220> FEATURE:
<223> OTHER INFORMATION: probe HBV B

<400> SEQUENCE: 107
ttgtcctggt tatcgctg                                                  18

<210> SEQ ID NO 108
<211> LENGTH: 19
<212> TYPE: DNA
<213> ORGANISM: artificial
<220> FEATURE:
<223> OTHER INFORMATION: probe HBV C

<400> SEQUENCE: 108
gtcctccaat tgtcctgg                                                  19

<210> SEQ ID NO 109
<211> LENGTH: 18
<212> TYPE: DNA
<213> ORGANISM: artificial
<220> FEATURE:
<223> OTHER INFORMATION: probe HBV D

<400> SEQUENCE: 109
ttgtcctggt tatcgctg                                                  18

<210> SEQ ID NO 110
<211> LENGTH: 19
<212> TYPE: DNA
<213> ORGANISM: artificial
<220> FEATURE:
<223> OTHER INFORMATION: probe HBV E

<400> SEQUENCE: 110
gtcctccaat tgtcctgg                                                  19

<210> SEQ ID NO 111
<211> LENGTH: 19
<212> TYPE: DNA
<213> ORGANISM: artificial
<220> FEATURE:
<223> OTHER INFORMATION: probe HBV F

<400> SEQUENCE: 111
caacttgtcc tggctatcg                                                 19

<210> SEQ ID NO 112
<211> LENGTH: 19
<212> TYPE: DNA
<213> ORGANISM: artificial
<220> FEATURE:
<223> OTHER INFORMATION: probe HBV G

<400> SEQUENCE: 112
```
caacttgtcc tggctatcg					19

<210> SEQ ID NO 113
<211> LENGTH: 19
<212> TYPE: DNA
<213> ORGANISM: artificial
<220> FEATURE:
<223> OTHER INFORMATION: probe HBV H

<400> SEQUENCE: 113
caacttgtcc tggctatcg					19

<210> SEQ ID NO 114
<211> LENGTH: 19
<212> TYPE: DNA
<213> ORGANISM: artificial
<220> FEATURE:
<223> OTHER INFORMATION: probe Chinese hamster

<400> SEQUENCE: 114
aaagcaccta taatcttat					19

<210> SEQ ID NO 115
<211> LENGTH: 19
<212> TYPE: DNA
<213> ORGANISM: artificial
<220> FEATURE:
<223> OTHER INFORMATION: probe Canine

<400> SEQUENCE: 115
aagtcaaaat acaacatca					19

<210> SEQ ID NO 116
<211> LENGTH: 19
<212> TYPE: DNA
<213> ORGANISM: artificial
<220> FEATURE:
<223> OTHER INFORMATION: probe Feline

<400> SEQUENCE: 116
cagtcgaaag tactacatc					19

<210> SEQ ID NO 117
<211> LENGTH: 19
<212> TYPE: DNA
<213> ORGANISM: artificial
<220> FEATURE:
<223> OTHER INFORMATION: probe Green monkey

<400> SEQUENCE: 117
actaatactt gcaattgac					19

<210> SEQ ID NO 118
<211> LENGTH: 21
<212> TYPE: DNA
<213> ORGANISM: artificial
<220> FEATURE:
<223> OTHER INFORMATION: probe Mouse

<400> SEQUENCE: 118
aagtaaaatc aacatatctt a					21

<210> SEQ ID NO 119
<211> LENGTH: 20
<212> TYPE: DNA

```
<213> ORGANISM: artificial
<220> FEATURE:
<223> OTHER INFORMATION: probe Rat

<400> SEQUENCE: 119
atacttacac acactaattc                                              20

<210> SEQ ID NO 120
<211> LENGTH: 19
<212> TYPE: DNA
<213> ORGANISM: artificial
<220> FEATURE:
<223> OTHER INFORMATION: probe cynomolgus monkey

<400> SEQUENCE: 120
actaacaccc ataattgat                                               19

<210> SEQ ID NO 121
<211> LENGTH: 19
<212> TYPE: DNA
<213> ORGANISM: artificial
<220> FEATURE:
<223> OTHER INFORMATION: probe Guinean pig

<400> SEQUENCE: 121
cgaagtttaa atcaccaat                                               19

<210> SEQ ID NO 122
<211> LENGTH: 19
<212> TYPE: DNA
<213> ORGANISM: artificial
<220> FEATURE:
<223> OTHER INFORMATION: probe SV40 TAg

<400> SEQUENCE: 122
ctcaacattc tactcctcc                                               19

<210> SEQ ID NO 123
<211> LENGTH: 18
<212> TYPE: DNA
<213> ORGANISM: artificial
<220> FEATURE:
<223> OTHER INFORMATION: probe SV40 VP1

<400> SEQUENCE: 123
accacagtgc ttcttgat                                                18

<210> SEQ ID NO 124
<211> LENGTH: 18
<212> TYPE: DNA
<213> ORGANISM: artificial
<220> FEATURE:
<223> OTHER INFORMATION: probe SV40 VP3

<400> SEQUENCE: 124
ccctggacaa cttcctttt                                               18

<210> SEQ ID NO 125
<211> LENGTH: 19
<212> TYPE: DNA
<213> ORGANISM: artificial
<220> FEATURE:
<223> OTHER INFORMATION: probe Y-chromosome, mouse

<400> SEQUENCE: 125
accaacagca gcagcagtt                                               19
```

```
<210> SEQ ID NO 126
<211> LENGTH: 19
<212> TYPE: DNA
<213> ORGANISM: artificial
<220> FEATURE:
<223> OTHER INFORMATION: probe Y-chromosome, human/monkey

<400> SEQUENCE: 126
cagctaggcc acttaccgc                                               19

<210> SEQ ID NO 127
<211> LENGTH: 19
<212> TYPE: DNA
<213> ORGANISM: artificial
<220> FEATURE:
<223> OTHER INFORMATION: probe Y-chromosome, rat

<400> SEQUENCE: 127
agaagggctt actacatac                                               19

<210> SEQ ID NO 128
<211> LENGTH: 19
<212> TYPE: DNA
<213> ORGANISM: artificial
<220> FEATURE:
<223> OTHER INFORMATION: probe HSV1 (HHV1)

<400> SEQUENCE: 128
tgttcaccac gagtacctg                                               19

<210> SEQ ID NO 129
<211> LENGTH: 19
<212> TYPE: DNA
<213> ORGANISM: artificial
<220> FEATURE:
<223> OTHER INFORMATION: probe HSV2 (HHV2)

<400> SEQUENCE: 129
tgtttaacgc gcgcacctg                                               19

<210> SEQ ID NO 130
<211> LENGTH: 19
<212> TYPE: DNA
<213> ORGANISM: artificial
<220> FEATURE:
<223> OTHER INFORMATION: probe VZV (HHV3)

<400> SEQUENCE: 130
tgcacgggtg cggaacgtt                                               19

<210> SEQ ID NO 131
<211> LENGTH: 19
<212> TYPE: DNA
<213> ORGANISM: artificial
<220> FEATURE:
<223> OTHER INFORMATION: probe CMV (HHV5)

<400> SEQUENCE: 131
acagaccgtt gcggctggc                                               19

<210> SEQ ID NO 132
<211> LENGTH: 19
<212> TYPE: DNA
<213> ORGANISM: artificial
<220> FEATURE:
```

```
<223> OTHER INFORMATION: probe HHV6

<400> SEQUENCE: 132
gcacttccgt cgtcgttct                                              19

<210> SEQ ID NO 133
<211> LENGTH: 19
<212> TYPE: DNA
<213> ORGANISM: artificial
<220> FEATURE:
<223> OTHER INFORMATION: probe HHV7

<400> SEQUENCE: 133
gccaacgtca tttcatttt                                              19

<210> SEQ ID NO 134
<211> LENGTH: 19
<212> TYPE: DNA
<213> ORGANISM: artificial
<220> FEATURE:
<223> OTHER INFORMATION: probe HHV8

<400> SEQUENCE: 134
atgtcacgat cgacagcgt                                              19

<210> SEQ ID NO 135
<211> LENGTH: 22
<212> TYPE: DNA
<213> ORGANISM: artificial
<220> FEATURE:
<223> OTHER INFORMATION: probe HIV1_M,N

<400> SEQUENCE: 135
atctataaaa gatggataat cc                                          22

<210> SEQ ID NO 136
<211> LENGTH: 23
<212> TYPE: DNA
<213> ORGANISM: artificial
<220> FEATURE:
<223> OTHER INFORMATION: probe HIV1_M

<400> SEQUENCE: 136
ctgtcatggg taccagcaca caa                                         23

<210> SEQ ID NO 137
<211> LENGTH: 20
<212> TYPE: DNA
<213> ORGANISM: artificial
<220> FEATURE:
<223> OTHER INFORMATION: probe HIV1_O

<400> SEQUENCE: 137
cttacatggg ttcctgccca                                             20

<210> SEQ ID NO 138
<211> LENGTH: 20
<212> TYPE: DNA
<213> ORGANISM: artificial
<220> FEATURE:
<223> OTHER INFORMATION: probe HIV1_N

<400> SEQUENCE: 138
ctctcttggg tacctgcaca                                             20
```

```
<210> SEQ ID NO 139
<211> LENGTH: 17
<212> TYPE: DNA
<213> ORGANISM: artificial
<220> FEATURE:
<223> OTHER INFORMATION: probe HIV1_N

<400> SEQUENCE: 139
gttgctatta tgtctat                                                17

<210> SEQ ID NO 140
<211> LENGTH: 17
<212> TYPE: DNA
<213> ORGANISM: artificial
<220> FEATURE:
<223> OTHER INFORMATION: probe HIV1_O

<400> SEQUENCE: 140
gatgctaata tgtctat                                                17

<210> SEQ ID NO 141
<211> LENGTH: 19
<212> TYPE: DNA
<213> ORGANISM: artificial
<220> FEATURE:
<223> OTHER INFORMATION: probe HIV2

<400> SEQUENCE: 141
aagaaataca attcctcca                                              19

<210> SEQ ID NO 142
<211> LENGTH: 19
<212> TYPE: DNA
<213> ORGANISM: artificial
<220> FEATURE:
<223> OTHER INFORMATION: probe SIV

<400> SEQUENCE: 142
aagaaataca atttcaaca                                              19

<210> SEQ ID NO 143
<211> LENGTH: 17
<212> TYPE: DNA
<213> ORGANISM: artificial
<220> FEATURE:
<223> OTHER INFORMATION: probe HIV2_2A/SIV

<400> SEQUENCE: 143
gtggtcaaga gacaaca                                                17

<210> SEQ ID NO 144
<211> LENGTH: 17
<212> TYPE: DNA
<213> ORGANISM: artificial
<220> FEATURE:
<223> OTHER INFORMATION: probe HIV2_2U/B

<400> SEQUENCE: 144
gtggtcaaaa gacaaca                                                17

<210> SEQ ID NO 145
<211> LENGTH: 19
<212> TYPE: DNA
<213> ORGANISM: artificial
<220> FEATURE:
<223> OTHER INFORMATION: probe EBV (HHV4)
```

```
<400> SEQUENCE: 145
agataaaagt ccccgggtg                                              19

<210> SEQ ID NO 146
<211> LENGTH: 19
<212> TYPE: DNA
<213> ORGANISM: artificial
<220> FEATURE:
<223> OTHER INFORMATION: probe sus

<400> SEQUENCE: 146
aaattaccat aacatcact                                              19

<210> SEQ ID NO 147
<211> LENGTH: 19
<212> TYPE: DNA
<213> ORGANISM: artificial
<220> FEATURE:
<223> OTHER INFORMATION: probe bos

<400> SEQUENCE: 147
tcactctatc gctcattga                                              19

<210> SEQ ID NO 148
<211> LENGTH: 19
<212> TYPE: DNA
<213> ORGANISM: artificial
<220> FEATURE:
<223> OTHER INFORMATION: probe rabbit

<400> SEQUENCE: 148
attataatca taaattgac                                              19

<210> SEQ ID NO 149
<211> LENGTH: 23
<212> TYPE: DNA
<213> ORGANISM: artificial
<220> FEATURE:
<223> OTHER INFORMATION: primer rabbit_f

<400> SEQUENCE: 149
cgaatgattt tagcctagac cca                                         23

<210> SEQ ID NO 150
<211> LENGTH: 24
<212> TYPE: DNA
<213> ORGANISM: artificial
<220> FEATURE:
<223> OTHER INFORMATION: primer rabbit_b

<400> SEQUENCE: 150
acttgttccg ttgatcaaat tatt                                        24

<210> SEQ ID NO 151
<211> LENGTH: 23
<212> TYPE: DNA
<213> ORGANISM: artificial
<220> FEATURE:
<223> OTHER INFORMATION: primer G. pig_f

<400> SEQUENCE: 151
cgaatgatat tagcctagat cca                                         23

<210> SEQ ID NO 152
<211> LENGTH: 24
```

```
<212> TYPE: DNA
<213> ORGANISM: artificial
<220> FEATURE:
<223> OTHER INFORMATION: primer G. pig_b

<400> SEQUENCE: 152
ttggtccgtt gatcaaaagg aatt                                          24

<210> SEQ ID NO 153
<211> LENGTH: 23
<212> TYPE: DNA
<213> ORGANISM: artificial
<220> FEATURE:
<223> OTHER INFORMATION: primer sus_f

<400> SEQUENCE: 153
ccgagtgatt ttaatctaga caa                                           23

<210> SEQ ID NO 154
<211> LENGTH: 23
<212> TYPE: DNA
<213> ORGANISM: artificial
<220> FEATURE:
<223> OTHER INFORMATION: primer sus_b

<400> SEQUENCE: 154
aacttgttcc gttgatcaaa att                                           23

<210> SEQ ID NO 155
<211> LENGTH: 23
<212> TYPE: DNA
<213> ORGANISM: artificial
<220> FEATURE:
<223> OTHER INFORMATION: primer bos_f

<400> SEQUENCE: 155
gagcgatttt aaagactaga ccc                                           23

<210> SEQ ID NO 156
<211> LENGTH: 23
<212> TYPE: DNA
<213> ORGANISM: artificial
<220> FEATURE:
<223> OTHER INFORMATION: primer bos_b

<400> SEQUENCE: 156
taacttgttc cgttgatcaa gtt                                           23

<210> SEQ ID NO 157
<211> LENGTH: 24
<212> TYPE: DNA
<213> ORGANISM: artificial
<220> FEATURE:
<223> OTHER INFORMATION: HHV6-b antisense

<400> SEQUENCE: 157
ccgtcatctt gtttacccat tcgt                                          24

<210> SEQ ID NO 158
<211> LENGTH: 24
<212> TYPE: DNA
<213> ORGANISM: artificial
<220> FEATURE:
<223> OTHER INFORMATION: Adeno_b antisense

<400> SEQUENCE: 158
```
actccggtcc ttctaacaca cctc                                                  24

<210> SEQ ID NO 159
<211> LENGTH: 24
<212> TYPE: DNA
<213> ORGANISM: artificial
<220> FEATURE:
<223> OTHER INFORMATION: Smrv_env_b antisense

<400> SEQUENCE: 159
tatctccaac cccagcctag ccca                                                  24

<210> SEQ ID NO 160
<211> LENGTH: 22
<212> TYPE: DNA
<213> ORGANISM: artificial
<220> FEATURE:
<223> OTHER INFORMATION: HSV1_b antisense

<400> SEQUENCE: 160
tttgctgccc gcgaggaggg cg                                                    22

<210> SEQ ID NO 161
<211> LENGTH: 25
<212> TYPE: DNA
<213> ORGANISM: artificial
<220> FEATURE:
<223> OTHER INFORMATION: Y_mouse_b antisense

<400> SEQUENCE: 161
gcattcttat ggcatttaat cgatg                                                 25

<210> SEQ ID NO 162
<211> LENGTH: 24
<212> TYPE: DNA
<213> ORGANISM: artificial
<220> FEATURE:
<223> OTHER INFORMATION: EBV_b antisense

<400> SEQUENCE: 162
catacggtca gtccatctcc ttca                                                  24

<210> SEQ ID NO 163
<211> LENGTH: 25
<212> TYPE: DNA
<213> ORGANISM: artificial
<220> FEATURE:
<223> OTHER INFORMATION: Myco_b2 antisense

<400> SEQUENCE: 163
gagcatgtgg tttaatttga agata                                                 25

<210> SEQ ID NO 164
<211> LENGTH: 23
<212> TYPE: DNA
<213> ORGANISM: artificial
<220> FEATURE:
<223> OTHER INFORMATION: Y_mouse_b antisense

<400> SEQUENCE: 164
atcagttcca tgaccacccc cag                                                   23

```
<210> SEQ ID NO 165
<211> LENGTH: 24
<212> TYPE: DNA
<213> ORGANISM: artificial
<220> FEATURE:
<223> OTHER INFORMATION: Rat_b antisense

<400> SEQUENCE: 165
tatcacaaat tgggctaatc tata                                              24
```

COMPOSITION COMPRISING AN OLIGONUCLEOTIDE MIXTURE FOR THE DETECTION OF CONTAMINATIONS IN CELL CULTURES

The present invention relates to a method for determining contaminations in a cell culture sample comprising the steps of (a) contacting a sample of a cell culture suspected to comprise contaminations with a composition comprising oligonucleotides under conditions which allow for amplification of polynucleotides, wherein said oligonucleotides comprise oligonucleotides of at least three different groups of oligonucleotides, and (b) determining the contaminations based on the amplified polynucleotides obtained by using the oligonucleotide groups of step (a). Moreover, the invention relates to a composition comprising an oligonucleotide mixture. Further encompassed by the present invention is a composition comprising a probe oligonucleotide mixture. Finally, the present invention also relates to kits comprising said oligonucleotide mixtures.

Contamination of eukaryotic cell cultures with microbial organisms as well as with other eukaryotic cell lines remains a major problem in cell culture related research. Although the contamination of cell cultures has been known for more than 50 years now, it is still a widespread cause for erroneous research results, for a reduced reproducibility and even for unusable therapeutic products. In the worst scenario, contamination with a microbial organism or cross-contamination with other eukaryotic lines may lead to diminished cell growth and may result in the loss of cultures.

*Mycoplasma* belong to the class Mollicutes and are frequently found in cell cultures as a contaminant. About 15% to 35% of all cell lines are infected with a limited number of *Mycoplasma* species predominantly of human, swine or bovine origin (Uphoff et al., 2002, In Vitro Cell Dev Biol Anim. 38(2):7985). A frequent cause for *Mycoplasma* contaminations are contaminated cell culture medium ingredients or careless working. Due to their small cell size, *Mycoplasma* are difficult to detect with a conventional microscope. *Mycoplasma* can affect most cellular functions such as inhibition of cell proliferation and protein biosynthesis, alteration of immunological reactions, virus proliferation and microarray gene expression profiles. Therefore, specific methods are required to detect *Mycoplasma* in a cell culture. *Mycoplasma* usually do not overgrow cell cultures. However, since *Mycoplasma* lack a cell wall, some antibiotics (e.g. ampicillin) are not effective to suppress *Mycoplasma* growth in cell culture.

Recently, SMRV (squirrel monkey retrovirus) was found to be a widespread cause for cell contamination. E.g., it was found that cells used for commercial production of interferon were contaminated with SMRV. SMRV was originally isolated from a lung tissue of the squirrel monkey *Saimiri sciureus* more than 30 years ago. The virus belongs to the class of endogenous type D retroviruses and is classified in biological risk group 2. Infection of other organisms is not described but since contamination of numerous vertebrate cell systems were described, an infection can not be excluded. Therefore, the German Central Commission for Biological Safety (ZKBS) recommends testing of all used cell lines for SMRV. Contaminated cell lines must either be eliminated or used under conditions of biological safety level 2 or higher.

Cross-contamination of cell cultures with other permanent cell lines cultivated in parallel is not infrequent. One of the known most frequent causes of such cross-contamination of cell cultures is contamination with HeLa cells. HeLa cells are derived from cervical adenocarcinoma cells that are infected with the human papillomavirus 18 (HPV-18). They are frequently used in medical research. Therefore, they are passed on from lab to lab, where practitioners did not always exercise stringent controls and/or were oblivious to cross-contamination as a problem. Moreover, since HeLa cells proved to be very robust in cell culture, they were capable of overgrowing many other cells present in the same culture.

Cell lines cultured from primary explants or subcultures after passage 1 can be endogenously infected with herpes, hepatitis and other viruses, as well as possible bacterial pathogens. This may represent a real and present source for human infection. Persons receiving primary or subsequent cultures of human lymphocytes, fetal cell mixtures, or hepatocytes may be obtaining human cells that contain human viruses including hepatitis and herpes viruses and even HIV. If not carefully tested by sensitive techniques contaminated cell lines pose a major threat to any personnel using it.

Contaminated cell cultures should never be used in research that demands a specific cell line and, therefore, should be generally discarded. The problem caused by contaminated cell lines can be mainly solved by an appropriate quality control including the analysis for cell cross-contamination in every cell culture laboratory. However, since the possible sources of cell culture contamination are numerous including viral and bacterial contamination as well as inter- or intraspecies contamination between various cell lines, the contaminations are difficult to assess.

A number of different methods for detecting contaminants in cell cultures have already been described and include, e.g. PCR, RNA hybridization, microscopic analysis and microbiological colony assay. However, the assays established for cell culture testing usually only detect a single source for cell contamination such as *Mycoplasma* or HeLa cells. Specifically, several commercial kits exist in the market to detect *Mycoplasma*. These tests are based not only on PCR amplification and subsequent read-out by e.g. gel electrophoresis but also on culturing cells in different media, DAPI staining, DNA hybridisation, and antibodies for specific *Mycoplasma* species. Among the PCR tests, several kits exist including e.g. the PCR *Mycoplasma* Test Kit from AppliChem, the PCR *Mycoplasma* Test Kit from MD Biosciences Inc., the Venor®GeM-*Mycoplasma* Detection Kit from Minerva Biolabs and many more. All these PCR tests rely on a precise PCR program with specific annealing and elongation temperatures and the specific primer compositions to achieve maximal sensitivity and specificity.

Concerning the detection of HeLa contaminations, HPV genotyping tests could be applied. Among these e.g. the Amplicor® test from Roche and the INNO-LiPA® HPV Genotyping Extra from Innogenetics apply strict PCR protocols and subsequent hybridisation to probes coupled to membranes.

Hepatitis B detection mostly relies on antibody detection against HBsAg, but can also be done by a variety of different tests including e.g. the real-time PCR-based Artus® HBV LC PCR Kit from Qiagen, the COBAS® AmpliScreen HBV Test from Roche, and the INNO-LiPA HBV Genotyping kit from Innogenetics. As for *Mycoplasma* and HBV detection, these tests rely on precise PCR protocols.

No human herpes virus kit is commercially available to genotype all HHV1 to 8. For SMRV and SV40 (VP1, Tag, VP3) detection, no commercial kits are yet available. Inter-species cross-contamination can be analysed by isoenzyme analysis or mitochondrial cytochrome b PCR-RFLP, but no commercial kit is available. Thus, while enabling to detect specific contaminations, known assays fail to assess numerous other possible contaminants simultaneously.

Thus, the technical problem underlying the present invention may be seen as the provision of means and methods for reliably determining a plurality of contaminations in cell cultures simultaneously without the drawbacks as referred to above. The technical problem is solved by the embodiments characterized in the claims and herein below.

Accordingly, the present invention relates to a method for determining contaminations in a cell culture sample comprising the steps of a) contacting a sample of a cell culture suspected to comprise contaminations with a composition comprising oligonucleotides of at least three different groups of oligonucleotides, said groups being selected from aa) an oligonucleotide group comprising at least one pair of oligonucleotides capable of specifically amplifying polynucleotides comprised by the squirrel monkey retrovirus (SMRV), wherein said at least one pair is selected from the following pairs of oligonucleotides
  i) a pair of oligonucleotides having a nucleic acid sequence as shown in SEQ ID NO:1 and SEQ ID NO:2 (oligonucleotides for amplification of SMRV gag), and
  ii) a pair of oligonucleotides having a nucleic acid sequence as shown in SEQ ID NO:3 and SEQ ID NO:4 (oligonucleotides for amplification of SMRV env); and
  iii) at least one pair of oligonucleotides which are capable of specifically amplifying polynucleotides which are amplified by the oligonucleotides of (i) and/or (ii), bb) an oligonucleotide group comprising at least one pair of oligonucleotides capable of specifically amplifying polynucleotides comprised by different *Mycoplasma* species, wherein said at least one pair is selected from the following pairs of oligonucleotides
  i) a pair of oligonucleotides having a nucleic acid sequence as shown in SEQ ID NO:5 and SEQ ID NO:6 and (oligonucleotides for amplification of the 16S RNA gene of different *Mycoplasma* species, Myco I)
  ii) a pair of oligonucleotides having a nucleic acid sequence as shown in SEQ ID NO:7 and SEQ ID NO:8 and (oligonucleotides for amplification of the 16S RNA gene of different *Mycoplasma* species, Myco II)
  iii) at least one pair of oligonucleotides which are capable of specifically amplifying polynucleotides which are amplified by the oligonucleotides of (i) and/or (ii), cc) an oligonucleotide group comprising at least one pair of oligonucleotides capable of specifically amplifying polynucleotides comprised by HeLa cells wherein said at least one pair is selected from the following pairs of oligonucleotides
  i) a pair of oligonucleotides having a nucleic acid sequence as shown in SEQ ID NO:9 and SEQ ID NO:10 (oligonucleotides for amplification of the E7 gene of HPV-18, Hela)
  ii) a pair of oligonucleotides which are capable of specifically amplifying polynucleotides which are amplified by the oligonucleotides of (i), dd) an oligonucleotide group comprising at least one pair of oligonucleotides capable of specifically amplifying polynucleotides comprised by adenovirus, wherein said at least one pair is selected from the following pairs of oligonucleotides
  i) a pair of oligonucleotides having a nucleic acid sequence as shown in SEQ ID NO:11 and SEQ ID NO:12 (oligonucleotides for amplification of different adenovirus genotypes) and
  ii) a pair of oligonucleotides which are capable of specifically amplifying polynucleotides which are amplified by the oligonucleotides of (i), ee) an oligonucleotide group comprising at least one pair of oligonucleotides capable of specifically amplifying polynucleotides comprised by *A. laidwaii* wherein said at least one pair is selected the following pairs of oligonucleotides
  i) a pair of oligonucleotides having a nucleic acid sequence as shown in SEQ ID NO:13 and SEQ ID NO:14 (oligonucleotides for amplification of the 16S RNA gene of *Acholeplasma*) and
  ii) a pair of oligonucleotides which are capable of specifically amplifying polynucleotides which are amplified by the oligonucleotides of (i), ff) an oligonucleotide group comprising at least one pair of oligonucleotides capable of specifically amplifying polynucleotides for a mammalian globin, wherein said at least one pair is selected the following pairs of oligonucleotides
  i) a pair of oligonucleotides having a nucleic acid sequence as shown in SEQ ID NO:15 and SEQ ID NO:16 (oligonucleotides for amplification of a human globin gene)
  ii) a pair of oligonucleotides having a nucleic acid sequence as shown in SEQ ID NO:17 and SEQ ID NO:18 (oligonucleotides for amplification of a mouse globin gene)
  iii) a pair of oligonucleotides having a nucleic acid sequence as shown in SEQ ID NO:19 and SEQ ID NO:20 (oligonucleotides for amplification of a rat globin gene); and
  iiii) at least one pair of oligonucleotides which are capable of specifically amplifying polynucleotides which are amplified by the oligonucleotides of (i), (ii) and/or (iii), gg) an oligonucleotide group comprising at least one pair of oligonucleotides capable of specifically amplifying polynucleotides comprised by different hepatitis B virus (HBV) strains wherein said at least one pair is selected the following pairs of oligonucleotides
  i) a pair of oligonucleotides having a nucleic acid sequence as shown in SEQ ID NO:21 and SEQ ID NO:22 (oligonucleotides for amplification of different HBV species), and
  ii) a pair of oligonucleotides which are capable of specifically amplifying polynucleotides which are amplified by the oligonucleotides of (i), hh) an oligonucleotide group comprising at least one pair of oligonucleotides capable of specifically amplifying polynucleotides comprised by a herpes virus wherein said at least one pair is selected from the following pairs of oligonucleotides
  i) a pair of oligonucleotides having a nucleic acid sequence as shown in SEQ ID NO:23 and SEQ ID NO:24 (oligonucleotides for amplification of the UL42 gene of HSV1),
  ii) a pair of oligonucleotides having a nucleic acid sequence as shown in SEQ ID NO:25 and SEQ ID NO:26 (oligonucleotides for amplification of the UL42 gene of HSV2), iii) a pair of oligonucleotides having a nucleic acid sequence as shown in SEQ ID NO:27 and SEQ ID NO:28 (oligonucleotides for amplification of the UL42 gene of HHV3), iiii) a pair of oligonucleotides having a nucleic acid sequence as shown in SEQ ID NO:29 and SEQ ID NO:30 (oligonucleotides for amplification of the UL42 gene of HHV4), iiiii) a pair of oligonucleotides having a nucleic acid sequence as shown in SEQ ID NO:31 and SEQ ID NO:32 (oligonucleotides for amplification of the UL42 gene of HHV5), iiiiii) a pair of oligonucleotides having a nucleic acid sequence as shown in SEQ ID NO:33 and SEQ ID NO:34 (oligonucleotides for amplification of the UL42 gene of HHV6), iiiiiii) a pair of oligonucleotides having a nucleic acid sequence as shown in SEQ ID NO:35 and SEQ ID NO:36 (oligonucleotides for amplification of the Pp41 gene of HHV7), and iiiiiiii) a pair of oligonucleotides having a nucleic acid sequence as shown in SEQ ID NO:37 and SEQ ID NO:38 (oligonucleotides for amplification of the UL42 gene of HHV8), and iiiiiiiii) at least one pair of oligonucleotides which are capable of specifically amplifying polynucleotides which are amplified by the oligonucleotides of (i), (ii), (iii), (iiii), (iiiii), (iiiiii), (iiiiiii) and/or (iiiiiiii), jj) an oligonucleotide group comprising at least one pair of oligonucleotides capable of specifically amplifying polynucleotides comprised by a mammalian Y chromosome wherein said at least one pair is selected from the following pairs of oligonucleotides i) a pair of oligonucleotides having a nucleic acid sequence as shown in SEQ ID NO:39 and SEQ ID NO:40 (oligonucleotides for amplification of a polynucleotide of the human Y chromosome), ii) a pair of oligonucleotides having a nucleic acid sequence as shown in SEQ ID NO:41 and SEQ ID NO:42 (oligonucleotides for amplification of a polynucleotide of the rat Y chromosome), iii) a pair of oligonucleotides having a nucleic acid sequence as shown in SEQ ID NO:43 and SEQ ID NO:44 (oligonucleotides for amplification of a polynucleotide of the mouse Y chromosome), and iiii) at least one pair of oligonucleotides which are capable of specifically amplifying polynucleotides which are amplified by the oligonucleotides of (i), (ii) and/or (iii), and kk) an oligonucleotide group comprising at least one pair of oligonucleotides capable of specifically amplifying polynucleotides comprised by SV40 (simian virus 40), wherein said at least one pair is selected from the following pairs of oligonucleotides i) a pair of oligonucleotides having a nucleic acid sequence as shown in SEQ ID NO:45 and SEQ ID NO:46 (oligonucleotides for amplification of the vp1 of SV40), ii) a pair of oligonucleotides having a nucleic acid sequence as shown in SEQ ID NO:47 and SEQ ID NO:48 (oligonucleotides for amplification of SV40 Tag), iii) a pair of oligonucleotides having a nucleic acid sequence as shown in SEQ ID NO:49 and SEQ ID NO:50 (oligonucleotides for amplification of vp3 of SV40), and iiii) at least one pair of oligonucleotides which are capable of specifically amplifying polynucleotides which are amplified by the oligonucleotides of (i), (ii) and/or (iii), and b) determining the contaminations in said sample based on the amplified polynucleotides obtained in step a).

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for confirmation of contaminations in a cell culture sample. The method may be carried out manually or assisted by automation. Preferably, step (a) and/or (b) may in total or in part be assisted by automation, e.g., by suitable robotic and sensory equipment for the determination in step (b).

The term "contamination" as used herein, preferably, relates to any unwanted microorganisms or eukaryotic cells that are present in a cell culture sample. A microorganism in the context of the present invention, preferably, is a bacterium or a virus. Bacterial contaminations are, preferably, contaminations with *Mycoplasma* and *Acholeplasma laidlawii*. Contaminations with *Mycoplasma* are, preferably, contaminations with *Mycoplasma* strains *M. arginini, M. fermentans, M. orale, M. hyorhinis, M. hominis, M. salivarium, M. synoviae, M. pirum, M. gallisepticum, M. pneumoniae*, and *Acholeplasma laidlawii*. Viral contaminations are, preferably, contaminations with SMRV (squirrel monkey retrovirus), contaminations with human papilomvirus 18, contaminations with a human herpes virus including herpes simplex virus 1 (HSV1), herpes simplex virus 2 (HSV2), Epstein-Barr virus (EBV), Varizella Zoster virus (VZV), Cytomegalie virus (CMV), HHV 6, 7, and/or 8 (HHV: human herpes virus), contaminations with HBV (hepatitis B virus) including genotypes A-H, contaminations with adenovirus 1, 2, 5, and/or 6, contaminations with human and simian immunodeficiency viruses HIV/SIV), and contaminations with SV40 (simian vacuolating virus 40).

A contamination with eukaryotic cells is herein also referred to as cross contamination. Contaminations with eukaryotic cells include, preferably, contaminations with any unwanted eukaryotic cells and, more preferably, with any unwanted mammalian cells. Even more preferably, such a contamination is a contamination with human cells, monkey cells (green monkey or cynomolgus monkey), mouse cells, rat cells, Chinese hamster cells, feline cells, rabbit cells, Guinean pig cells, cow cells, pig cells or canine cells. Moreover, it is also contemplated that a cross-contamination is by cells of a different chromosomal sex, thus male cells instead of female cells and vice versa. Such a cross-contamination, preferably, can be assessed by using oligonucleotides that are specific for the Y-chromosome.

Also contemplated by the present invention is a contamination with HeLa cells. HeLa cells are well known in the art and are frequently used in research. Said cells are human immortal cells derived from cervical cancer cells and contain the human papillomavirus 18 (HPV-18) genome. Since HeLa cells are commonly used cell lines and since they grow very rapidly, they can outgrow other cells within the same cell culture and, thus, are a frequent contaminant in cell cultures.

Other contaminations, preferably, can be assessed by detecting specific viral DNA sequences that are permanently present in a host cell. In addition to natural infection, such intracellular viral sequences can originate from experimental introduction into cell lines either by transfection of recombinant nucleic acids containing viral sequences such as promoters, enhancers, splice and polyadenylation signal sequences or by experimental infection using transforming viruses such as EBV or SV40 to immortalize cells in order to obtain stably growing cell lines. Specifically, some frequently used cell lines are known to comprise DNA of viral origin, e.g. as already mentioned above HeLa cells comprise HPV-18, HEK293T cells comprise DNA of Adenovirus 5 and SV40 (more examples can be found herein elsewhere), whereas other cell lines are free of certain virus-derived DNA. Therefore, an oligonucleotide pair capable of amplifying certain viral sequences allows differentiating whether a respective contamination is present in a cell culture sample.

It is to be understood that in case of cross-contamination the wanted cells may not be present at all in the cell culture that is analyzed by the method of the present invention, e.g. due to a putative mix up of the cell cultures samples in the past, or due to a contamination of the cell culture sample in the past by eukaryotic cells that outgrew the cells that were originally present in a cell culture sample.

The term "contacting" as used in the context of the method of the present invention is understood by the skilled person. Preferably, the term relates to bringing a composition of the present invention in physical contact with a sample and thereby, e.g. allowing the sample and the composition to interact.

The term "cell culture sample", preferably, relates to a sample of cells which are maintained in vitro in a suitable cultivation medium. Preferably, said cells are eukaryotic cells, more preferably mammalian cells and most preferably mouse, rat, feline, canine, bovine, rabbit, Guinean pig, pig, Chinese hamster, monkey or human cells. Preferably, the sample may have any volume deemed appropriate. Moreover, the sample may have been further processed in order to carry out the method of the present invention. Particularly, polynucleotides such as DNA or RNA, preferably DNA, might be extracted and/or purified from the obtained sample by methods and means known in the art (e.g., see Examples). Thus, the term sample also may relate to polynucleotides, preferably DNA, purified and/or extracted from any sample as mentioned to above. A particularly preferred method for the preparation of DNA from a cell culture is by centrifugation of a suitable volume of the cell culture, resuspending the pellet in a suitable buffer, such as phosphate-buffered saline (PBS) or an other buffer suitable for PCR amplification, incubating the cell suspension at a high temperature such as 95° C., followed by a centrifugation step in order to allow removal of the cell debris. The, thus, obtained supernatant comprising extracted DNA can be analyzed in the method of the present invention. Moreover, prior to the analysis said supernatant can be stored at low temperatures such as −20° C.

A sample of a cell culture suspected to comprise contaminations may be any sample of cultivated eukaryotic cells, preferably of cultivated mammalian cells. It is to be understood that said cells have been specifically prepared for cultivation or have been cultivated in vitro prior to analysing them by the method of the present invention. Thus, the sample may also be a primary cell culture which can be analyzed by the method of the present invention in order to assess the cells/contaminations present in said primary cell culture.

The sample may comprise more than one contamination, i.e. a plurality of contaminations. Preferably, sample comprises at least one contamination. At least one means one or more than one, at least two, at least three, at least four, at least five, at least six, at least seven, at least eight, at least nine, at least ten or more contaminations. However, a sample suspected to comprise contaminations may also turn out to be free of contamination, i.e. does not comprise any contamination that can be detected by applying the method of the present invention.

The term "composition comprising oligonucleotides" as used herein relates to a composition comprising oligonucleotide molecular species wherein all molecules of the molecular species have a specific nucleic acid sequence. Preferably, the term "oligonucleotide" relates to a primer for DNA amplification techniques such as PCR (whereas the term "probe oligonucleotides", preferably, relates to probes, see herein below). An oligonucleotide shall comprise a number of nucleotides being sufficient for specific binding to a sequence stretch of a target polynucleotide. Preferably, an oligonucleotide as meant herein has between 15 and 30 nucleotides in length, more preferably between 18 and 28 nucleotides in length, and most preferably between 23-25 nucleotides in length. Preferably, the sequence of the oligonucleotide is not degenerated. Preferably, the oligonucleotide is a single-stranded oligodesoxyribonucleotide. However, due to self-complementarity the oligonucleotide may be partially double-stranded under certain conditions (depending on, e.g., the sequence of the oligonucleotide, the salt concentration and the temperature). Particularly preferred oligonucleotides have the specific sequences and/or properties referred to herein.

The oligonucleotides of the present invention, preferably, are used as a starting molecule for the synthesis of a polynucleotide which is sufficiently complementary to the nucleic acid strand to be copied by an appropriate amplification technique, preferably by PCR, for polynucleotides.

The oligonucleotides of the present invention may be labelled or contain other modifications which allow a detection and/or analysis of an amplification product and/or the binding to a carrier. Labelling can be done by various techniques well known in the art and depending of the label to be used. Particularly, the oligonucleotides may be biotinylated in order to enable the binding of the amplification products to a streptavidin surface or fluorescent conjugate. Moreover, labels to be used in the context of the present invention may be, but are not limited to, fluorescent labels comprising, inter alia, fluorochromes such as R-phycoerythrin, Cy3, Cy5, fluorescein, rhodamin, Alexa, or Texas Red. However, the label may also be an enzyme or an antibody. It is envisaged that an enzyme to be used as a label will generate a detectable signal by reacting with a substrate. Suitable enzymes, substrates and techniques are well known in the art. An antibody to be used as label may specifically recognize a target molecule which can be detected directly (e.g., a target molecule which is itself fluorescent) or indirectly (e.g., a target molecule which generates a detectable signal, such as an enzyme). The oligonucleotides of the present invention may also contain 5' restriction sites, locked nucleic acid molecules (LNA) or be part of a peptide nucleotide acid molecule (PNA). Such PNA can be, in principle, detected via the peptide part by, e.g., antibodies.

The term "composition comprising oligonucleotides" as meant herein relates to a mixture of different oligonucleotide molecular species, preferably of oligonucleotide groups as specified elsewhere in this application. In addition, a composition may comprise further components other than the oligonucleotides, e.g. components for the amplification of polynucleotides of polynucleotides, preferably by polymerase chain reaction (PCR). Such components may be, but are not limited to, an aqueous buffer, a water soluble magnesium salt, deoxythymidine triphosphate (dTTP), deoxyadenosine triphosphate (dATP), deoxycitidine triphosphate (dCTP) and deoxyguanosine triphosphate, (dGTP) and a DNA polymerase, e.g. the thermostable DNA polymerase from *Thermus aquaticus*.

The term "oligonucleotide group" as used herein, preferably, relates to a composition comprising a plurality of oligonucleotide pairs. However, it is also contemplated that an oligonucleotide group may only comprise one oligonucleotide pair. Preferably, an oligonucleotide group is specific for one type of contamination (belonging to the same phylogenetic tree), e.g. for a contamination with *Mycoplasma* or a contamination with HHV species, different *Mycoplasma* species or various adenoviral species.

The term "at least three oligonucleotide groups", preferably, relates to three or more than three oligonucleotide groups, thus at least three, four, five, six, seven, eight, nine oligonucleotide groups or more.

The term "oligonucleotides pair", preferably, relates to two oligonucleotides capable of amplifying polynucleotides that are specific for a contamination. The sequences of the oligonucleotides as well as the corresponding targets and probe oligonucleotides are shown also shown in table 1.

The term "pair of oligonucleotides capable of specifically amplifying polynucleotides comprised by the squirrel monkey retrovirus (SMRV)", preferably relates to a pair of oligonucleotides capable of amplifying a polynucleotide encoding (i) the gag gene (GenBank Accession Number NC_001514.1) of SMRV or (ii) the env gene (GenBank Accession Number NC_001514.1) of SMRV. It is to be understood, that in the context of the method of the present invention also parts of the respective genes may be amplified. Preferably, for (i) the pair of oligonucleotides have a nucleic acid sequence as shown in SEQ ID NO:1 and SEQ ID NO:2 (i.e. said pairs comprises an oligonucleotide having a nucleic acid sequence as shown in SEQ ID NO:1, and an oligonucleotide having a nucleic acid sequence as shown in SEQ ID NO:2) (oligonucleotides for amplification of SMRV gag), and for (ii) the oligonucleotides have a nucleic acid sequence as shown in SEQ ID NO:3 and SEQ ID NO:4 (oligonucleotides for amplification of SMRV env). Preferably, the term also relates to pairs of oligonucleotides which are capable of specifically amplifying polynucleotides which are amplified by the aforementioned oligonucleotide pairs, thus the pairs mentioned in (i) or (ii).

The term "pair of oligonucleotides capable of specifically amplifying polynucleotides comprised by different *Mycoplasma*", preferably relates to a pair of oligonucleotides capable of amplifying a polynucleotide encoding (i) the 16S ribosomal RNA gene of the following *Mycoplasma* species *M. arginini* (GenBank Accession Number U15794.1), *M. fermentans* (GenBank Accession Number M24289.1), *M. orale* (GenBank Accession Number AY796060.1), *M. hyorhinis* (GenBank Accession Number AF412982.1), *M. hominis* (GenBank Accession Number M96660.1), *M. salivarium* (GenBank Accession Number AF125583.1), *M. synoviae* (GenBank Accession Number X52083.1), *M. gallisepticum* (GenBank Accession Number NC_004829.1), or (ii) the 16S ribosomal RNA gene of the following *Mycoplasma* species *M. pirum* (GenBank Accession Number M23940.1) and *M. pneumoniae* (GenBank Accession Number AF132741.1), or parts thereof. Preferably, for (i) the pair of oligonucleotides has a nucleic acid sequence as shown in SEQ ID NO:7 and SEQ ID NO:8 (oligonucleotides for amplification of the 16S RNA gene of different *Mycoplasma* species, Myco I), and for (ii) a pair of oligonucleotides has a nucleic acid sequence as shown in SEQ ID NO:5 and SEQ ID NO:6 (oligonucleotides for amplification of the 16S RNA gene of different *Mycoplasma* species Myco II). Preferably, the term also relates to pairs of oligonucleotides which are capable of specifically amplifying polynucleotides which are amplified by the aforementioned oligonucleotide pairs, thus the pairs mentioned in (i) or (ii).

The term "pair of oligonucleotides capable of specifically amplifying polynucleotides comprised by *A. laidwaii*", preferably relates to a pair of oligonucleotides capable of amplifying a polynucleotide encoding the 16S ribosomal RNA gene (GenBank Accession Number AY740437.1) of *A. laidwaii*. Preferably, the pair of oligonucleotides has a nucleic acid sequence as shown in SEQ ID NO:13 and SEQ ID NO:14 (oligonucleotides for amplification of the 16S RNA gene of *Acholeplasma*). Preferably, the term also relates to pairs of oligonucleotides which are capable of specifically amplifying polynucleotides which are amplified by the aforementioned oligonucleotide pair.

The term "pair of oligonucleotides capable of specifically amplifying polynucleotides comprised by HeLa cells", preferably relates to a pair of oligonucleotides capable of amplifying a polynucleotide that is originally derived from HPV18 (human papillomavirus) which is stably integrated into the genome of HeLa cells. Preferably, the pair of oligonucleotides has a nucleic acid sequence as shown in SEQ ID NO:9 and SEQ ID NO:10 (oligonucleotides for amplification of the E7 gene of HPV-18, Hela). Preferably, the term also relates to pairs of oligonucleotides which are capable of specifically amplifying polynucleotides which are amplified by the aforementioned oligonucleotide pair.

The term "pair of oligonucleotides capable of specifically amplifying polynucleotides comprised by adenovirus", preferably relates to a pair of oligonucleotides capable of amplifying a polynucleotide derived from adenovirus 1, 2, 5 or 6 encoding the E1A gene. It is to be understood that said polynucleotide may be stably integrated into the genomic DNA of a eukaryotic host cell line. Eukaryotic host cell lines known to comprise adenoviral 5 DNA, preferably, are HEK293 and HEK293T. Preferably, the pair of oligonucleotides has a nucleic acid sequence as shown in SEQ ID NO:11 and SEQ ID NO:12 (oligonucleotides for amplification of different adenovirus genotypes). Preferably, the term also relates to pairs of oligonucleotides which are capable of specifically amplifying polynucleotides which are amplified by the aforementioned oligonucleotide pairs.

The term "pair of oligonucleotides capable of specifically amplifying polynucleotides for a globin gene", preferably relates to a pair of oligonucleotides capable of amplifying a polynucleotide comprised by a beta-globin gene, preferably of a mammalian globin gene and, more preferably, of a rat, human and mouse globin gene. Preferably, said pair of oligonucleotides has a nucleic acid sequence as shown in (i) SEQ ID NO:15 and SEQ ID NO:16 for the human globin (oligonucleotides for amplification of a human globin gene), (ii) in SEQ ID NO:17 and SEQ ID NO:18 for mouse globin (oligonucleotides for amplification of a mouse globin gene), or (iii) in SEQ ID NO:19 and SEQ ID NO:20 for rat globin (oligonucleotides for amplification of a rat globin gene). Preferably, the term also relates to pairs of oligonucleotides which are capable of specifically amplifying polynucleotides which are amplified by the aforementioned oligonucleotide pairs.

The term "pair of oligonucleotides capable of specifically amplifying polynucleotides comprised by hepatitis B virus (HBV) strains", preferably relates to a pair of oligonucleotides capable of amplifying a polynucleotide derived from various hepatitis B virus strains/genotypes encoding the protein S gene. It is well known in the art that the genomic region comprising said polynucleotide is highly conserved. Therefore, said pair of polynucleotides allows the detection of various HBV strains including genotypes A to G. It is to be understood that said polynucleotide may be stably integrated into the genomic DNA of a eukaryotic host cell line. A eukaryotic host cell line known to comprise HBV DNA, preferably, is the liver cancer cell line Alexander (IFO50069). Preferably, for (i) the pair of oligonucleotides has a nucleic acid sequence as shown in SEQ ID NO:21 and SEQ ID NO:22 (oligonucleotides for amplification of different HBV species). Preferably, the term also relates to pairs of oligonucleotides which are capable of specifically amplifying polynucleotides which are amplified by the aforementioned oligonucleotide pairs, thus the pairs mentioned in (i).

The term "pair of oligonucleotides capable of specifically amplifying polynucleotides comprised by a herpes virus", preferably relates to a pair of oligonucleotides capable of amplifying a polynucleotide derived from human herpes virus 1, 2, 3, 4, 5, 6, 7 and 8, respectively (Human herpes simplex virus 1, HSV1, frequently also referred to as HHV1, Human herpes simplex virus 2, HSV2, frequently also referred to as HHV2, Varicella Zoster Virus, VZV, frequently also referred to as HHV3, Epstein Barr virus, EBV, frequently also referred to as HHV4, Cytomegalovirus, CMV, frequently also referred to as HHV5, HHV6, HHV7 and HHV8 frequently also referred to as Kaposi's sarcoma-associated herpesvirus, encoding a gene of the UL42 or UL44 families. It is to be understood that said polynucleotide may be stably present in a eukaryotic cell line. Eukaryotic host cell lines known to comprise EBV (HHV4), preferably, are Namalwa, P3HR1, or B95-8. Preferably, the pair of oligonucleotides for HSV1 has a nucleic acid sequence as shown in SEQ ID NO:23 and SEQ ID NO:24 (oligonucleotides for amplification of the UL42 gene of HSV1), for HSV2 a nucleic acid sequence as shown in SEQ ID NO:25 and SEQ ID NO:26 (oligonucleotides for amplification of the UL42 gene of HSV2), for HHV3 a nucleic acid sequence as shown in SEQ ID NO:27 and SEQ ID NO:28 (oligonucleotides for amplification of the UL42 gene of HSV3), for HHV4 a nucleic acid sequence as shown in SEQ ID NO:29 and SEQ ID NO:30 (oligonucleotides for amplification of the UL42 gene of HSV4), for HHV5 a nucleic acid sequence as shown in SEQ ID NO:31 and SEQ ID NO:32 (oligonucleotides for amplification of the UL42 gene of HSV5), for HHV6 a nucleic acid sequence as shown in SEQ ID NO:33 and SEQ ID NO:34 (oligonucleotides for amplification of the UL42 gene of HSV6), for HHV7 a nucleic acid sequence as shown in SEQ ID NO:35 and SEQ ID NO:36 (oligonucleotides for amplification of the UL42 gene of HSV7), and for HHV8 a nucleic acid sequence as shown in SEQ ID NO:37 and SEQ ID NO:38 (oligonucleotides for amplification of the UL42 gene of HSV8). Preferably, the term also relates to pairs of oligonucleotides which are capable of specifically amplifying polynucleotides which are amplified by the aforementioned oligonucleotide pairs.

The term "pair of oligonucleotides capable of specifically amplifying polynucleotides comprised by a mammalian Y chromosome", preferably relates to a pair of oligonucleotides capable of amplifying a polynucleotide comprised by a mammalian Y chromosome, preferably of the (i) human, (ii) rat and (iii) mouse sex determining region of Y chromosome (Sry), respectively. Preferably, said pair of oligonucleotides has a nucleic acid sequence as shown in SEQ ID NO:39 and SEQ ID NO:40 for (i), and SEQ ID NO:41 and SEQ ID NO:42 for (ii), and SEQ ID NO:43 and SEQ ID NO:44 for (iii). Preferably, the term also relates to pairs of oligonucleotides which are capable of specifically amplifying polynucleotides which are amplified by the aforementioned oligonucleotide pairs.

The term "pair of oligonucleotides capable of specifically amplifying polynucleotides comprised by SV40 (simian virus 40)", preferably relates to a pair of oligonucleotides capable of amplifying a polynucleotide derived from SV40 (J02400) encoding (i) the vp1 gene, (ii) the T-antigen, and (iii) the vp3 gene, respectively. It is to be understood that said polynucleotide may be stably integrated into the genomic DNA of a eukaryotic host cell line. Eukaryotic host cell lines known to comprise SV40 DNA, preferably, are HEK293T or cos7. HEK293T cells are known to contain vp1 and T-antigen sequences, while vp1, T-antigen and vp3 sequences are found in Cos7. Moreover, many DNA vectors that are used to transfect cell lines contain SV40 elements, such as the poly-A signal found in vp1 or splice sites found in the T-antigen. Therefore, a detection of vp1 and/or T-antigen may also be due to a transfection with such vectors or due to the contamination with a cell line transfected with one of these vectors. Preferably, for (i) the pair of oligonucleotides has a nucleic acid sequence as shown in SEQ ID NO:45 and SEQ ID NO:46 (oligonucleotides for amplification of vp1 of SV40). Preferably, for (ii) the pair of oligonucleotides has a nucleic acid sequence as shown in SEQ ID NO:47 and SEQ ID NO:48 (oligonucleotides for amplification of SV40 tag). Preferably, for (iii) the pair of oligonucleotides (vp3) has a nucleic acid sequence as shown in SEQ ID NO:49 and SEQ ID NO:50 (oligonucleotides for amplification of the vp3 of SV40). Preferably, the term also relates to pairs of oligonucleotides which are capable of specifically amplifying polynucleotides which are amplified by the aforementioned oligonucleotide pairs.

The amount and/or the concentration of the oligonucleotides may be any amount or concentration deemed appropriate. The amounts and/or concentrations of the individual oligonucleotides of the invention may differ and, thus, a solution comprising said oligonucleotides may not be equimolar with respect to the oligonucleotides. Preferred concentrations of the oligonucleotides in a solution suitable for the amplification of polynucleotides can be found in the Examples. A particularly preferred concentration of each oligonucleotide is between 0.5 and 5 µM, more preferably 1 and 4 µM, most preferable 2 and 3 µM. Moreover, it is to be understood that the person skilled in the art is able to adjust the concentrations of the oligonucleotides of the invention in order to optimize the amplification of specific polynucleotides as referred to herein and, thus, to optimize the detection of contaminations in a cell culture without further ado.

The term "under conditions which allow for amplification of polynucleotides" as used herein is understood by the skilled person. The term relates to a template-dependent process which results in an increase of the amount of a nucleic acid molecule relative to its initial amount. In accordance with the present invention the amplification of a polynucleotide of interest shall allow its detection by any method deemed appropriate and/or, e.g., described herein below. The amplification of a polynucleotide of interest may be carried out by well-known methods, preferably by polymerase chain reaction (PCR), but also by reverse transcriptase PCR, real-time PCR, reverse transcriptase real-time PCR, Templex-PCR, nucleic-acid sequence based amplification (NASBA), and isothermal amplification methods using polymerases and specific oligonucleotides as primers. The aforementioned amplification methods are well known in the art. Preferred embodiments of a PCR in the context of the present invention are described in the Examples.

The term "determining contaminations" as used herein relates to assessing the presence or absence of certain contaminating cells as referred to herein in a cell culture sample. Preferably, the contaminations are determined, and thus detected, simultaneously. The determination of contaminations is done by identifying amplified polynucleotides that are specific for the contaminations to be detected. Preferably, the amplification of polynucleotides that are specific for the respective contaminations is done in only one container, thus, in the same container. A preferred container is a reaction tube. Such reaction tubes well known in the art and, e.g., are commonly as referred to as PCR tubes. It is to be understood that the form of these tubes may depend on the PCR apparatus used for the amplification of contamination-specific oligonucleotides.

The determination of the contaminations is based on the amplified polynucleotides, and relates to identifying amplified polynucleotides that are specific for the various, individual contaminations. Preferably, this will be achieved by detecting the presence or absence of amplified polynucleotides that are specific for the contaminations to be detected. Methods of determining if an amplified polynucleotide is present or absent are well known in the art and preferably rely on the comparison of the amount and/or identity of the amplified polynucleotides to suitable controls, as exemplified in Example 10. Based on the determination contaminations can be identified. If an amplified polynucleotide that is specific for an individual contamination is present, then the respective contamination is present in the cell culture sample. If there is no amplification product for a polynucleotide that is specific for a certain contamination and, thus, if an amplified polynucleotide is absent, the respective contamination is not present in the tested cell culture sample. However, it is also to be understood that the amplification of certain polynucleotides also may indicate that a cell line comprises wanted cells. E.g. if cell culture samples are tested that should comprise human cells, an amplification of a human globin polynucleotide would indicate that said cell culture samples, indeed, comprise human cells.

The detection/identification of a plurality of amplified polynucleotides and, thus, of a plurality of contaminations can be done because of sequence variation between the amplified polynucleotides. Determining the contaminations based on the amplified polynucleotides is, preferably, done by using suitable probe oligonucleotides. Thus, the determination of the various amplified polynucleotides, preferably, comprises the step of hybridizing the amplified polynucleotides with probe polynucleotides that specifically bind to the amplified polynucleotides. A probe oligonucleotide in the context of the present invention, preferably, is single-stranded nucleic acid molecule that is specific for a polynucleotide that can be amplified by using the oligonucleotides according to the invention. The skilled person knows that a probe oligonucleotide comprises a stretch of nucleotides that specifically hybridize with the target, thus, is complementary to the target polynucleotide. Said stretch of nucleotides is, preferably, 85%, 90%, 95%, 99% or more preferably 100% identical to a sequence region comprised by a target polynucleotide. The degree of identity (percentage, %) between two or more nucleic acid sequences is, preferably, determined by the algorithms of Needleman and Wunsch or Smith and Waterman. To carry out the sequence alignments, the program PileUp (J. Mol. Evolution., 25, 351-360, 1987, Higgins 1989, CABIOS, 5: 151-153) or the programs Gap and BestFit (Needleman 1970, J. Mol. Biol. 48; 443-453 and Smith 1981, Adv. Appl. Math. 2; 482-489), which are part of the GCG software packet (Genetics Computer Group, 575 Science Drive, Madison, Wis., USA 53711, vers. 1991), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. Preferably, a probe oligonucleotide as meant herein is between 15 and 30 nucleotides in length, more preferably between 15 and 28 nucleotides in length, and most preferably between 18-23 nucleotides in length. Preferably, the probe oligonucleotides are bound to a carrier providing a solid surface. Preferably, said carrier is a small particle or bead. The overall size of a small particle or bead, preferably, may be in the micrometer or nanometer range. Preferably, said beads and particles may be stained with a specific dye, more preferably in with a specific fluorescent dye. Preferably, by staining various carriers with various dyes, the carries can be distinguished from each other. By using a carrier with a specific dye for a specific probe oligonucleotide (thus, a nucleic acid that targets the amplified polynucleotides of a specific contamination), said carrier is distinguishable from other carriers comprising different dyes. In one preferred embodiment commercially available Luminex microspheres (Luminex Corp., Austin, Tex., USA) are used. Thus, for determining contaminations the contamination-specific probes are coupled to fluorescence-labelled polystyrene beads (Luminex suspension array technology) which are hybridized with the amplification products under suitable, preferably, stringent conditions. Moreover, the amplification products may be identified by use of microarrays, Reverse-Line Blots (RLB), Dot blots or similar technologies which contain contamination specific probe oligonucleotides linked to a suitable carrier.

In another preferred embodiment of the current invention, one or more antisense oligonucleotide(s) to one or more oligonucleotide(s) is (are) comprised in the hybridisation assay. The antisense oligonucleotide, preferably, is an oligonucleotide with properties as specified above with the ability to specifically hybridize to an oligonucleotide. More preferably, the antisense oligonucleotide is an oligonucleotide with properties as specified above comprising the complementary sequence of an oligonucleotide. Methods to determine complementarity of nucleic acid sequences are well known in the art and rely on Watson-Crick rules for base pairing in nucleic acids. Most preferably, antisense oligonucleotides are oligonucleotides with properties as specified above comprising nucleic acid sequences as shown in SEQ ID No: 157 to 165.

Preferably, the probe oligonucleotides that specifically bind to the amplified polynucleotides are selected from the group consisting of probe oligonucleotides comprising a nucleic acid sequence as shown in SED ID NO: 78 (allows detection of the 16 S ribosomal RNA gene of *Mycoplasma orale* and, thus, of *Mycoplasma orale*), SED ID NO: 79 (allows detection of the 16 S ribosomal RNA gene of *Mycoplasma hyorhinis* and, thus, of *Mycoplasma hyorhinis*), SED ID NO: 80 (allows detection of the 16 S ribosomal RNA gene of *Mycoplasma arginini*, and, thus of *Mycoplasma arginini*), SED ID NO: 81 (allows detection of the 16 S ribosomal RNA gene of *Mycoplasma fermentans*, and, thus, of *Mycoplasma fermentans*) SED ID NO: 82 (allows detection of the 16 S ribosomal RNA gene of *Mycoplasma salivarium*, and, thus, of *Mycoplasma salivarium*), SED ID NO: 83 (allows detection of the 16 S ribosomal RNA gene of *Mycoplasma hominis* and, thus, of *Mycoplasma hominis*), SED ID NO: 84 (allows detection of the 16 S ribosomal RNA gene of *Mycoplasma synoviae*, and, thus, of *Mycoplasma synoviae*), SED ID NO: 85 (allows detection of the 16 S ribosomal RNA gene of *Mycoplasma gallisepticum*, and, thus of *Mycoplasma gallisepticum*), SED ID NO: 86 (allows detection of the 16 S ribosomal RNA gene of *Mycoplasma orale, Mycoplasma*

*hyorhinis, Mycoplasma arginini, Mycoplasma fermentans, Mycoplasma salivarium, Mycoplasma hominis, Mycoplasma synoviae*, and *Mycoplasma gallisepticum*) SED ID NO: 87 (allows detection of the 16 S ribosomal RNA gene of *Mycoplasma pneumoniae* and, thus, of *Mycoplasma pneumoniae*), SED ID NO: 88 (allows detection of the 16 S ribosomal RNA gene of *Mycoplasma pirum*, and, thus, of *Mycoplasma pirum*), SED ID NO: 89 (allows detection of the 16 S ribosomal RNA gene of *M. pirum* and *M. pneumoniae*, and, thus, of *M. pirum* and *M. pneumoniae*), SED ID NO: 90 (allows detection of the 16 S ribosomal RNA gene of *A. laidlawii*, and, thus, of *A. laidlawii*), SED ID NO:91 (allows detection of the 16 S ribosomal RNA gene of *A. granularum*, and, thus, of *A. granularum*), SEQ ID NO:92 (allows detection of the E7 gene of HPV18 and, thus, of HeLa cells), SEQ ID NO:93 (allows detection of the rat beta globin gene and, thus, of rat cells), SEQ ID NO:94 (allows detection of the mouse beta globin major gene, and, thus, of mouse cells), SEQ ID NO:95 (allows detection of the cynomolgus beta globin chain gene, and, thus, of cynomolgus cells), SEQ ID NO:96 (allows detection of the human beta globin chain gene, and, thus, of human cells), SEQ ID NO:97 (allows detection of human and monkey beta globin chain gene, and, thus, of human and monkey cells.), SEQ ID NO:98 (allows detection of the Pol-A gene of different mammalian and vertebrate cells (see above), SEQ ID NO:99 (allows detection of the E1A gene of Adenovirus 1 and 2, and, thus of Adenovirus 1 and 2), SEQ ID NO:100 (allows detection of the E1A gene of Adenovirus 5, and, thus of Adenovirus 5), SEQ ID NO:101 (allows detection of the E1A gene of Adenovirus 6, and, thus of Adenovirus 6), SEQ ID NO:102 (allows detection of the E1A gene of Adenovirus 1, 2, 5 and 6, and, thus of Adenovirus 1, 2, 5 and 6), SEQ ID NO:103 (allows detection of the gag gene of SMRV and, thus, of SMRV), SEQ ID NO:104 (allows detection of the env gene of SMRV and, thus, of SMRV), SEQ ID NO:105 (allows detection of the protein S gene of HBV A, and, thus of HBV A), SEQ ID NO:106 (allows detection of the protein S gene of HBV A and B, and, thus of HBV A and B), SEQ ID NO:108 (allows detection of the protein S gene of HBV C, and, thus of HBV C), SEQ ID NO:109 (allows detection of the protein S gene of HBV D, and, thus of HBV D), SEQ ID NO:110 (allows detection of the protein S gene of HBV E, and, thus of HBV E), SEQ ID NO:111 (allows detection of the protein S gene of HBV F, and, thus of HBV F), SEQ ID NO:112 (allows detection of the protein S gene of HBV G, and, thus of HBV G), SEQ ID NO:113 (allows detection of the protein S gene of HBV H, and, thus of HBV H), SEQ ID NO:114 (allows detection of the 16 S ribosomal gene of Chinese hamster cells, and, thus, of Chinese hamster cells), SEQ ID NO:115 (allows detection of the 16 S ribosomal gene of canine cells, and, thus, of canine cells), SEQ ID NO:116 (allows detection of the 16 S ribosomal gene of feline cells, and, thus, of feline cells), SEQ ID NO:117 (allows detection of the 16 S ribosomal gene of Green monkey cells, and, thus, of Green monkey cells), SEQ ID NO:118 (allows detection of the 16 S ribosomal gene of mouse cells, and, thus, of mouse cells), SEQ ID NO:119 (allows detection of the 16 S ribosomal gene of rat cells, and, thus, of rat cells), SEQ ID NO:120 (allows detection of the 16 S ribosomal gene of cynomolgus monkey cells, and, thus, of cynomolgus monkey cells), SEQ ID NO:121 (allows detection of the 16 S ribosomal gene of Guinean pig cells, and, thus, of Guinean pig cells), SEQ ID NO:148 (allows detection of the 16 S ribosomal gene of rabbit cells, and, thus, of rabbit cells), SEQ ID NO:146 (allows detection of the 16 S ribosomal gene of pig cells, and, thus, of pig cells), SEQ ID NO:147 (allows detection of the 16 S ribosomal gene of bovine cells, and, thus, of bovine cells), SEQ ID NO:122 (allows detection of the T-Antigen of SV40, and, thus, of SV40), SEQ ID NO:123 (allows detection of the VP1 gene of SV40, and, thus, of SV40), SEQ ID NO:124 (allows detection of the VP3 gene of SV40, and, thus, of SV40), SEQ ID NO:125 (allows detection of the Y chromosome of mouse cells, and, thus of male mouse cells), SEQ ID NO:126 (allows detection of the Y chromosome of human and monkey cells, and, thus of male human and monkey cells), SEQ ID NO:127 (allows detection of the Y chromosome of rat cells, and, thus of male rat cells), SEQ ID NO:128 (allows detection of the UL42 gene of HHV1, and, thus, of HHV1 (or cells comprising HHV1)), SEQ ID NO:129 (allows detection of the UL42 gene of HHV2, and, thus, of HHV2), SEQ ID NO:130 (allows detection of the UL42 gene of HHV3, and, thus, of HHV3), SEQ ID NO:145 (allows detection of the UL42 gene of HHV4, and, thus, of HHV4), SEQ ID NO:131 (allows detection of the UL42 gene of HHV5, and, thus, of HHV5), SEQ ID NO:132 (allows detection of the pp41 gene of HHV6, and, thus, of HHV6), SEQ ID NO:133 (allows detection of the UL42 gene of HHV7, and, thus, of HHV7), SEQ ID NO:134 (allows detection of the UL42 gene of HHV8, and, thus, of HHV8), SEQ ID NO:135 (allows detection of the gag gene of HIV 1 group M and N, and, thus, of HIV 1 group M and N), SEQ ID NO:136 (allows detection of the pol gene of HIV 1 group M, and, thus, of HIV 1 group M), SEQ ID NO:137 (allows detection of the pol gene of HIV 1 group O, and, thus, of HIV 1 group O) SEQ ID NO:138 (allows detection of the pol gene of HIV 1 group N, and, thus, of HIV 1 group N), SEQ ID NO:139 (allows detection of the gag gene of HIV 1 group N, and, thus, of HIV 1 group N), SEQ ID NO:140 (allows detection of the gag gene of HIV 1 group O, and, thus, of HIV 1 group O), SEQ ID NO:141 (allows detection of the pol gene of HIV 2, and, thus, of HIV 2), SEQ ID NO:142 (allows detection of the pol gene of SIV, and, thus, of SIV), SEQ ID NO:143 (allows detection of the env gene of HIV group 2A and SIV, and, thus, of HIV group 2A and SIV), and SEQ ID NO:144 (allows detection of the env gene of HIV group 2U and 2B, and, thus, of HIV group 2U and 2B). Thus, the probe oligonucleotides that specifically bind to the amplified polynucleotides are, preferably, selected from the group consisting of probe oligonucleotides comprising a nucleic acid sequence as shown in SED ID NO: 78 to SEQ ID 144. Preferably, the probe oligonucleotides that specifically bind to the amplified polynucleotides are selected from the group consisting of probe oligonucleotides comprising a nucleic acid sequence as shown in SED ID NO: (SEQ ID No. 78 to 119, and SEQ ID No. 121 to 134, and SEQ ID No. 145 to 148).

The nucleic acid sequences of the probe oligonucleotides as well as the contaminants/cells that are detected by using said probe oligonucleotides are listed in table 1. Also shown in table 1 are the corresponding amplified polynucleotides as well as the oligonucleotide pairs that amplify these polynucleotides.

However, it is also contemplated by the present invention that the amplification products are identified by other methods known in the art. The identification may be done by sequencing amplification product(s) and or by RFLP (restriction fragment length polymorphism) analysis. The determination of contaminations can also be done by conducting microarray assays, southern blot assays, dot blot assays, or by membrane-based reverse line blot.

In a specific embodiment of the method of the present invention, the composition comprising oligonucleotides further comprises oligonucleotides capable of amplifying a fragment of the polymerase A (PolA) polynucleotide, wherein said oligonucleotides bind to highly conserved regions of the PolA-polynucleotide.

The polA polynucleotide encodes for polymerase alpha (Ultraconserved Elements in the Human Genome, Bejerano et al., 2004) The polA polynucleotide is highly conserved between mammals and other vertebrates (e.g. in chicken and frog). Preferably, oligonucleotides capable of amplifying a fragment of the polymerase A (PolA) polynucleotide, preferably, allow for specifically amplifying a fragment or part of the polA polynucleotide of mammals, and more preferably, of the human, chimpanzee, mouse, rat, canine and feline polA polynucleotide.

The amplification of the polA polynucleotide, or of a fragment or part thereof, preferably, serves as an internal positive control. Therefore, the amplification of the polA polynucleotide allows for assessing errors that occurred, e.g., when preparing the template DNA for the analysis or when setting up the PCR reaction. Efficient amplification of the polA polynucleotide, preferably, indicates that the amplification reaction was successful and that the DNA is of sufficient quality, whereas inefficient amplification, preferably, indicates that an amplification reaction was not successful, e.g., due to an inappropriate sample or errors in the PCR setup. In the latter case, a PCR reaction may have to be repeated, e.g., with a freshly obtained sample and/or freshly purified DNA. Thus, the use of oligonucleotides that specifically amplify the polA polynucleotide, preferably, prevents false-negative results.

Preferably, the oligonucleotides capable of amplifying a fragment of the polymerase A (PolA) polynucleotide have a nucleic acid sequence as shown in SEQ ID NO:51 and SEQ ID NO:52 (oligonucleotides for amplification of the polA gene of different mammalian vertebrate cells).

In another preferred embodiments of the method of the present invention, the composition comprising oligonucleotides further comprises an oligonucleotide group that comprises at least one pair of oligonucleotides capable of specifically amplifying polynucleotides comprised by the mitochondrial DNA of various mammals, wherein said at least one pair is selected from the group of oligonucleotide group consisting of an oligonucleotide group comprising at least one pair of oligonucleotides capable of specifically amplifying polynucleotides comprised by a mitochondrial DNA of various mammals wherein said at least one pair is selected from the following pairs of oligonucleotides i) a pair of oligonucleotides having a nucleic acid sequence as shown in SEQ ID NO:53 and SEQ ID NO:54 (thus, oligonucleotides for the detection of Chinese hamster cells), ii) a pair of oligonucleotides having a nucleic acid sequence as shown in SEQ ID NO:55 and SEQ ID NO:56 (thus, oligonucleotides for the detection of canine cells), iii) a pair of oligonucleotides having a nucleic acid sequence as shown in SEQ ID NO:57 and SEQ ID NO:58 (thus, oligonucleotides for the detection of feline cells), iv) a pair of oligonucleotides having a nucleic acid sequence as shown in SEQ ID NO:59 and SEQ ID NO:60 (thus, oligonucleotides for the detection of Green monkey cells), v) a pair of oligonucleotides having a nucleic acid sequence as shown in SEQ ID NO:61 and SEQ ID NO:62 (thus, oligonucleotides for the detection of mouse cells), vi) a pair of oligonucleotides having a nucleic acid sequence as shown in SEQ ID NO:63 and SEQ ID NO:64 (thus, oligonucleotides for the detection of rat cells), and vii) a pair of oligonucleotides having a nucleic acid sequence as shown in SEQ ID NO:65 and SEQ ID NO:66 (thus, oligonucleotides for the detection of cynomolgus monkey cells), viii) a pair of oligonucleotides having a nucleic acid sequence as shown in SEQ ID NO:149 and SEQ ID NO:150 (thus, oligonucleotides for the detection of rabbit cells), ix) a pair of oligonucleotides having a nucleic acid sequence as shown in SEQ ID NO:151 and SEQ ID NO:152 (thus, oligonucleotides for the detection of Guinean pig cells), x) a pair of oligonucleotides having a nucleic acid sequence as shown in SEQ ID NO:153 and SEQ ID NO:154 (thus, oligonucleotides for the detection of pig cells), and xi) a pair of oligonucleotides having a nucleic acid sequence as shown in SEQ ID NO:155 and SEQ ID NO:156 (thus, oligonucleotides for the detection of bovine cells), and xii) at least one pair of oligonucleotides which are capable of specifically amplifying polynucleotides which are amplified by the oligonucleotides of (i), (ii), (iii), (iv), (v), (vi), (vii), (viii), (ix), (x) and/or (xi).

The term "pair of oligonucleotides capable of specifically amplifying polynucleotides for a mitochondrial DNA", preferably relates to pairs of oligonucleotides capable of amplifying a polynucleotide encoding a 16S ribosomal RNA gene of different species, preferably of a rat, mouse, Chinese hamster, canine, feline, green monkey, cynomolgus monkey, rabbit, Guinean pig, and pig 16S ribosomal RNA gene. Preferably, said pairs of oligonucleotides have a nucleic acid sequence as shown in (i) SEQ ID NO:63 and SEQ ID NO:64 for the rat 16S ribosomal RNA gene, (ii) in SEQ ID NO:61 and SEQ ID NO:62 for the mouse 16S ribosomal RNA gene, (iii) in SEQ ID NO:53 and SEQ ID NO:54 for Chinese hamster 16S ribosomal RNA gene, (iv) in SEQ ID NO:55 and SEQ ID NO:56 for canine 16S ribosomal RNA gene, (v) in SEQ ID NO:57 and SEQ ID NO:58 for feline 16S ribosomal RNA gene, (vi) in SEQ ID NO:59 and SEQ ID NO:60 for green monkey 16S ribosomal RNA gene, (vii) in SEQ ID NO:65 and SEQ ID NO:66 for cynomolgus monkey 16S ribosomal RNA gene, or (viii) in SEQ ID NO:149 and SEQ ID NO:150 for rabbit 16S ribosomal RNA gene, (ix) in SEQ ID NO:151 and SEQ ID NO:152 for Guinean pig 16S ribosomal RNA gene, (x) in SEQ ID NO:153 and SEQ ID NO:154 for pig ribosomal RNA gene, or (xi) in SEQ ID NO:155 and SEQ ID NO:156 for the bovine 16S ribosomal RNA gene. Preferably, the term also relates to pairs of oligonucleotides which are capable of specifically amplifying polynucleotides which are amplified by the aforementioned oligonucleotide pairs.

In another preferred embodiments of the method of the present invention, composition comprising oligonucleotides further comprises an oligonucleotide group that comprises at least one pair of oligonucleotides capable of specifically amplifying polynucleotides comprised by various HIV (human immunodeficiency virus) and SIV (simian immunodeficiency virus) strains, wherein said at least one pair is selected from the group of oligonucleotide group consisting of, i) a pair of oligonucleotides having a nucleic acid sequence as shown in SEQ ID NO:67 and SEQ ID NO:68 (oligonucleotides for amplification of HIV1 gag), ii) a pair of oligonucleotides having a nucleic acid sequence as shown in SEQ ID NO:69 and SEQ ID NO:71 (oligonucleotides for amplification of HIV1 pol), iii) a pair of oligonucleotides having a nucleic acid sequence as shown in SEQ ID NO:70 and SEQ ID NO:71 (oligonucleotides for amplification of HIV1 pol), iiii) a pair of oligonucleotides having a nucleic acid sequence as shown in SEQ ID NO:72 and SEQ ID NO:73 (oligonucleotides for amplification of HIV gag), iiiii) a pair of oligonucleotides having a nucleic acid sequence as shown in SEQ ID NO:74 and SEQ ID NO:75 (oligonucleotides for amplification of HIV and SIV pol), iiiiii) a pair of oligonucleotides having a nucleic acid sequence as shown in SEQ ID NO:76 and SEQ ID NO:77 (oligonucleotides for amplification of HIV/SIV env), and iiiiiii) at least one pair of oligonucleotides which are capable of specifically amplifying polynucleotides which are amplified by the oligonucleotides of (i), (ii), (iii), (iiii), (iiiii), and/or (iiiiii).

The term "pair of oligonucleotides capable of specifically amplifying polynucleotides comprised by various HIV and SIV strains", preferably relates to a pair of oligonucleotides capable of amplifying a polynucleotide comprised by the genome of various HIV strains, preferably of the (i) gag gene of HIV 1 group M and N, (ii) pol gene of HIV 1 group M, N, O, (iii) gag gene of HIV 1 group N and O, (iiii) pol gene of HIV 2 and SIV, and (iiiii) eng gene of HIV2 and SIV, respectively. Examples for HIV positive cell lines are, e.g. the T lymphoblastoid cell line 8E5 (NIH, ATCC 8993) or the T lymphoblastoid cell line H9/HTLV-IIIB (ATCC, CRL-8543). Preferably, said pair of oligonucleotides have a nucleic acid sequence as shown in SEQ ID NO:67 and SEQ ID NO:68 for (i), and SEQ ID NO:69, SEQ ID NO:70 and SEQ ID NO:71 (one forward primer and two backward primers, thus, two oligonucleotide pairs a) SEQ ID NO:69 and SEQ ID NO:71, b) SEQ ID NO:70 and SEQ ID NO:71) for (ii), SEQ ID NO:72 and SEQ ID NO:73 for (iii), and SEQ ID NO:74 and SEQ ID NO:75 for (iiii), and SEQ ID NO:76 and SEQ ID NO:77 for (iiiii). Preferably, the term also relates to pairs of oligonucleotides which are capable of specifically amplifying polynucleotides which are amplified by the aforementioned oligonucleotide pairs.

Advantageously, it was shown in the studies underlying the present invention that determining contaminations in a cell culture sample comprising the steps of contacting a cell culture sample with a composition comprising an oligonucleotides as referred to herein and detecting contaminations based on the amplified polynucleotides by applying said compositions is required for sufficient detection of contaminations in a cell culture sample. The method of the present invention is more reliable than the prior art since it allows the simultaneous determination of contaminations which can be microbial contaminations or cross-contamination with unwanted eukaryotic cell lines. The prior art does not teach the combined determination of contaminants as referred to herein. The method of the present invention, if applied, will be beneficial for basic research as well as for the commercial application of cell cultures since it allows a cost-effective and reliable determination of the most frequent contaminants of cell cultures. Moreover, by applying the method of the present invention it is possible to detect contaminants that are present in a cell culture sample to a very low extent. Therefore, the method of the present invention provides a very sensitive determination of various contaminants. Particularly, it was shown that SMRV was detected with less than 10 plasmid copy numbers, and that cell culture contaminations of less than 1 to 3 cells in a background of 6,000 cells per PCR reaction can be detected even if multiple contaminations are simultaneously present and tested for (Example 7). Moreover, it was demonstrated that multiple contaminations (Example 7) and all contaminations (Example 10) can be detected simultaneously. In artificial contamination simulation experiments it was shown that more than 16 PCR products (Example 7) and more than 40 PCR products (Figure 10) can be detected at the same time. It has to be understood that under natural conditions this number of contaminations is very unlikely to occur, however, suggests that the method can detect even more targets simultaneously and this without competition effects. Furthermore, and also advantageous is the use of oligonucleotides that are capable of amplifying a fragment of the PolA polynucleotide. The use of said oligonucleotides, e.g. may serve as a control of the quality of the template PCR as well as a control for assessing mistakes during the set-up of a PCR reaction.

The definitions made above apply mutatis mutandis to the following:

Moreover, the present invention also relates to a composition comprising oligonucleotides as referred to above.

The aforementioned composition is herein also referred to as "composition comprising an oligonucleotide mixture", or "composition comprising oligonucleotides"

Moreover, the aforementioned composition, preferably, further comprises oligonucleotides as referred to herein, e.g. a pair of oligonucleotides capable of amplifying a fragment of the polymerase A (PolA) polynucleotide. Moreover, said composition may further comprise oligonucleotides as referred to above, e.g. oligonucleotides that are capable of amplifying polynucleotides for mitochondrial DNA of various species (see above).

Furthermore, the present invention relates a composition comprising probe oligonucleotides, wherein said composition comprises at least five probe oligonucleotides selected from the group of probe oligonucleotides having a nucleic acid sequence as shown in SEQ ID NO: 78 to 148. At least five means five or more than five and, thus, at least six, at least seven, at least eight, at least ten, at least thirteen, at least fifteen, at least twenty or more. The aforementioned composition is herein also referred to as "composition comprising a probe oligonucleotide mixture".

Furthermore, the present invention also relates to the use of a composition of the present invention (thus, of a composition comprising an oligonucleotide mixture and/or a composition comprising a probe oligonucleotide mixture as specified above) for determining contaminations in a cell culture sample. Preferably, said contaminations are detected simultaneously. Said contaminations, preferably, are selected from the group consisting of SMRV (squirrel monkey retrovirus), *Mycoplasma* including *M. arginini, M. fermentans, M. orale, M. hyorhinis, M. hominis, M. salivarium, M. synoviae, M. pirum, M. gallisepticum, M. pneumoniae, A. laidlawii,* eukaryotic host cells comprising adenovirus 1, 2, 5 or 6 DNA, HeLa cells, human cells, rat cells, mouse cells, Chinese hamster cells, canine cells, feline cells, monkey cells, Guinean pig cells, rabbit cells, bovine cells, pig cells, male host cells, eukaryotic host cells comprising a herpes virus including HHV 1 to 8, human host cells comprising hepatitis B virus DNA including genotypes A to H, eukaryotic host cells comprising SV40 DNA, and eukaryotic host cells transfected with DNA vectors containing elements of SV40 (VP1 or T-Antigen). Other preferred contaminations are referred to elsewhere in this specification.

Finally, the present invention relates to a kit, preferably adapted for carrying out the method of the present invention, comprising the composition comprising an oligonucleotide mixture and/or the composition comprising a probe oligonucleotide mixture as specified herein and an instruction manual. Preferably, said kit further comprises the composition comprising a probe oligonucleotide mixture.

The term "kit" as used herein refers to a collection of the aforementioned means, e.g., means for contacting a sample under conditions which allow for amplification of polynucleotides and for determining contaminations based on the amplified polynucleotides, preferably, provided separately or within a single container. The container, also preferably, comprises instructions for carrying out the method of the present invention. The components of the kit are provided, preferably, in a "ready-to-use" manner, e.g., concentrations are adjusted accordingly, etc.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1

Multiplex Primer and Probe Design

The accession numbers of the various targets of the multiplex cell culture contamination PCR are listed in Table 1. All nucleotide sequences were obtained from the National Center for Biotechnology Information (NCBI) nucleotide sequence database (GenBank). The 16s RNA region of *Mycoplasma orale, M. hyorhinis, M. arginini, M. fermentans, M. salivarium, M. hominis, M. pneumoniae, M. synoviae, M. pirum, M. gallisepticum, Acholeplasma laidlawii*; the E1A region of Adenovirus 1, 2, 5, 6; and species-specific beta-globin genes were aligned with T-COFFEE (Notredame et al., 2000), respectively, in order to identify conserved sequences flanking inner polymorphic regions for primer design. Pools of oligonucleotides rather than the addition of degenerate base sites in the primer sequences were preferred to avoid synthesis variation in the primer sequence. In general, backward oligonucleotide primers were biotinylated for detection by hybridisation; exception: forward oligonucleotide primers SV40_VP3_f_ and HIV1_O/N_gag_f_ were biotinylated.

All primer sequences were assessed for primer-dimers formation and for unspecific annealing of biotinylated primers to oligonucleotide probes by using Fast-PCR (Kalendar, 2007, FastPCR: a PCR primer and probe design and repeat sequence searching software with additional tools for the manipulation and analysis of DNA and protein, www.biocenter.helsinki.fi/bi/programs/fastper.htm). All primers were tested in single- and multiplex PCR and subsequent gel electrophoresis or Luminex hybridisation (see Examples 2 and 10).

For each target gene and organism oligonucleotide probe sequences were chosen within polymorphic sequences amplified by primers mentioned above. Oligonucleotide probes were selected to be highly specific for the gene or organism of interest. All probe sequences were tested for unspecific hybridisation to biotinylated oligonucleotide primers by Fast-PCR and in Luminex hybridisation experiments.

TABLE 1

Probes polynucleotides and oligonucleotides (primer) overview

| Target (contaminating organism)/ Probe name | Probe oligonucleotide sequence 5' to 3' | Probe SEQ ID NO: | Region | Accession number | Primer name (F, forward; b, backward) | Primer sequence 5' to 3' | Primer SEQ ID NO: |
|---|---|---|---|---|---|---|---|
| M. pneumoniae | GGCGATCCCCTCGGTAGTGA | 87 | 16S ribosomal RNA gene | AF132741.1 | Myco_f1 | TGGGGAGCAAATAGGATT AGATACC | 5 |
| M. pirum | GGTAAACGCCTCGGTGTCGT | 88 | 16S ribosomal RNA gene | M23940.1 | Myco_b1 | GTACCGTCGAATTAAGCA ACATGCT | 6 |
| Myco-uni 2 | TACATTCGCAAGAATGAAAC TT | 89 | 16S ribosomal RNA gene | | | | |
| M. orale | TCGGTGGAAAACTACTGACG | 78 | 16S ribosomal RNA gene | AY796060.1 | Myco_f2 | TGGGGAGCAAACAGGATT AGATACC | 7 |
| M. hyorhinis | GGAATAATTTCACTAACGCA | 79 | 16S ribosomal RNA gene | AF412982.1 | Myco_b2 | TATCTTCAAATTAAACCA CATGCTC | 8 |
| M. arginini | GTGGAGAGTTCACTGACGCA | 80 | 16S ribosomal RNA gene | U15794.1 | | | |
| M. fermentans | CTGATGGGGAACTCATCGGC | 81 | 16S ribosomal RNA gene | M24289.1 | | | |
| M. salivarium | TCGGCAGAGAACTGTTGACG | 82 | 16S ribosomal RNA gene | AF125583.1 | | | |
| M. hominis | CGGTGGAGAATCACTGACGC | 83 | 16S ribosomal RNA gene | M96660.1 | | | |
| M. synoviae | TTGATAGAAACCATCGACGC | 84 | 16S ribosomal RNA gene | X52083.1 | | | |
| M. gallisepticum | TGTCGGAGCGAATACTTCG | 85 | 16S ribosomal RNA gene | NC_004829.1 | | | |
| Myco-uni 1 | GATCCGCCTGAGTAGTATG | 86 | 16S ribosomal RNA gene | | | | |
| A. laidlawii | ACTCAAACAAGTAACCACATA | 90 | 16S ribosomal RNA gene | AY740437.1 | Acholeplasma_f | GGGGATGGATCACCTCCT TTCTAA | 13 |
| A. granularum | GTACACTCAAACCTCATAAT | 91 | 16S ribosomal RNA gene | DQ400428.1 | Acholeplasma_b | CAAGCGAGTGCTCTAACC AACTGA | 14 |

TABLE 1-continued

Probes polynucleotides and oligonucleotides (primer) overview

| Target (contaminating organism)/ Probe name | Probe oligonucleotide sequence 5' to 3' | Probe SEQ ID NO: | Region | Accession number | Primer name (F, forward; b, backward) | Primer sequence 5' to 3' | Primer SEQ ID NO: |
|---|---|---|---|---|---|---|---|
| HPV18 | CAGACGACCTTCGAGCAT | 92 | E7 | NC_001357.1 | HPV_18_f | GACCTTCTATGTCACGAG CAATTA | 9 |
|  |  |  |  |  | HPV_18_b | TGCACACCACGGACACAC AAAG | 10 |
| Rat beta globin | ATATAAAGCAGAACAGAACC | 93 | beta-globin | X06701.1 | Bg_rat_f | AGCCTGTACCATAGCCAC CCTGAG | 19 |
|  |  |  |  |  | Bg_rat_b | CCTGAGGTTGCGAGTCAA CACAACAG | 20 |
| Mouse beta globin | ATATAAGGTGAGGTAGGATC | 94 | beta-globin major gene | J00413.1 | Bg_mouse_f | GCTGAGACGTCCTAAGCC AGTGAGT | 17 |
|  |  |  |  |  | Bg_mouse_b | TCTGGGGTTGTGAGTCAA CACAACTA | 18 |
| cynomolgus beta globin | CAAGGCAATAACCATACA | 95 | beta globin chain gene | X05665.1 | Bg_human/ monkey_f | TGACCAAATCAGGGTAAT TTTGCATT | 15 |
| Human beta globin | CAGGGCAATAATGATACA | 96 | beta globin chain gene | AY260740.1 | Bg_human/ monkey_b | AGAATGGTGCAAAGAGGC ATGATACA | 16 |
| Human/monkey beta globin | CTAATACTTTCCCTAATCTCT | 97 | beta globin chain gene |  |  |  |  |
| Mammal IC | GTACATCTGATTACTGAAGT AC | 98 | polymerase alpha (POLA) | e.g. NW_ 927700.1 | POLA_f | TCAGAAATAGTTCTTGAT CGGGTTTG | 51 |
|  |  |  |  |  | POLA_b | TAAATGCAGCTGCCTCTT TCAATGC | 52 |
| Adenovirus 1,2 | TCCTAAATTGGTGCCTGCT | 99 | E1A | AY490817.1, J01917.1 | Adeno_f | GTGTCTGAACCTGAGCCT GAGCC | 11 |
| Adenovirus 5 | GCCGTCCTAAAATGGCGCC | 100 | E1A | AY339865.1 | Adeno_b | GAGGTGTGTTAGAAGGAC CGGAGT | 12 |
| Adenovirus 6 | CCTGTGTCCAGAGAATG | 101 | E1A | AY490818.1 |  |  |  |
| Adenovirus 1,2,5,6 | GCAATAGTAGTACGGATAGC | 102 | E1A |  |  |  |  |
| SMRV | GGCCCTTGTAGAGAGTCTTA GTGAA | 103 | Gag | NC_001514.1 | Smrv_gag_f | TCAGAGCCCACCGAGCCT ACCTAC | 1 |
|  |  |  |  |  | Smrv_gag_b | CAGCGCAGCACGAGACAA GAAAA | 2 |
|  | TGCTTGATATTCTGTCAGCC ACCCA | 104 | Env | NC_001514.1 | Smrv_env_f | GGCGGACCCCAAGATGCT GTG | 3 |
|  |  |  |  |  | Smrv_env_b | TGGGCTAGGCTGGGGTTG GAGATA | 4 |
| HBV A | TTGTCCTGGTTATCGCTG, GTCCTCCAATTTGTCCTGG | 105 106 | Protein S gene | V00866.1 | HBV_f | GGTGGACTTCTCTCAATT TTCTAGG | 21 |
| HBV B | TTGTCCTGGTTATCGCTG | 107 | Protein S gene | M54923.1 | HBV_b | ATGATAAAACGCCGCAGA CACATC | 22 |
| HBV C | GTCCTCCAATTTGTCCTGG | 108 | Protein S gene | X75665.1 |  |  |  |
| HBV D | TTGTCCTGGTTATCGCTG | 109 | Protein S gene | X80924.1 |  |  |  |
| HBV E | GTCCTCCAATTTGTCCTGG | 110 | Protein S gene | X75657.1 |  |  |  |
| HBV F | CAACTTGTCCTGGCTATCG | 111 | Protein S gene | X75658.1 |  |  |  |
| HBV G | CAACTTGTCCTGGCTATCG | 112 | Protein S gene | AF160501.1 |  |  |  |
| HBV H | CAACTTGTCCTGGCTATCG | 113 | Protein S gene | AY090454.1 |  |  |  |
| Chinese hamster | AAAGCACCTATAATCTTAT | 114 | 16S ribosomal RNA gene | DQ334846.1 | CH f | CCGAATGATTATAGCTAA GGCAC | 53 |
|  |  |  |  |  | CH b | CTTGGTCCGTTGATCAAA TATGT | 54 |
| Dog/Canine | AAGTCAAAATACAACATCA | 115 | 16S ribosomal RNA gene | AY729880.1 | Dog_f | CCGAGTGATTAAAATTTA GACCC | 55 |
|  |  |  |  |  | Dog_b | TTGTTCCGTTGATCAAAA ATTAT | 56 |
| Cat/Feline | CAGTCGAAAGTACTACATC | 116 | 16S ribosomal RNA gene | U20753.1 | Cat_f | CCGAGTGATTTAAATCTA GACTA | 57 |
|  |  |  |  |  | Cat_b | CTTGTTCCGTTGATCAAG GTTTT | 58 |
| Green monkey | ACTAATACTTGCAATTGAC | 117 | 16S ribosomal RNA gene | AY863426.1 | Gree_mo_f | CGAACAATCCATGCTAAG ACTAC | 59 |
|  |  |  |  |  | Gree_mo_b | ACTTGTTCCATTGATCAA ATTATT | 60 |

TABLE 1-continued

Probes polynucleotides and oligonucleotides (primer) overview

| Target (contaminating organism)/ Probe name | Probe oligonucleotide sequence 5' to 3' | Probe SEQ ID NO: | Region | Accession number | Primer name (F, forward; b, backward) | Primer sequence 5' to 3' | Primer SEQ ID NO: |
|---|---|---|---|---|---|---|---|
| Mouse | AAGTAAAATCAACATATCTTA | 118 | 16S ribosomal RNA gene | V00711.1 | mouse_f | CCGAATGATTATAACCTAGACTT | 61 |
| | | | | | mouse_b | TGGTCCGTTGATCAAAATATATC | 62 |
| Rat | ATACTTACACACACTAATTC | 119 | 16S ribosomal RNA gene | DQ673917.1 | Rat_f | AATAAACAACTACAATCACTTAAC | 63 |
| | | | | | Rat_b | TATAGATTAGCCCAATTTGTGATA | 64 |
| Cynomolgus monkey | ACTAACACCCATAATTGAT | 120 | 16S ribosomal RNA gene | AF420036.1 | Cyno_f | CGAATAACACATGCCAAGACTAC | 65 |
| | | | | | Cyno_b | ACTTGTTCCGTTGATCAAATAATT | 66 |
| rabbit | ATTATAATCATAAATTGAC | 148 | 16S ribosomal RNA gene | AJ001588.1 | rabbit_f | CGAATGATTTTAGCCTAGACCCA | 149 |
| | | | | | rabbit_b | ACTTGTTCCGTTGATCAAATTATT | 150 |
| Guinean pig | CGAAGTTTAAATCACCAAT | 121 | 16S ribosomal RNA gene | AJ222767.1 | G. pig_f | CGAATGATATTAGCCTAGATCCA | 151 |
| | | | | | G. pig_b | TTGGTCCGTTGATCAAAAGGAATT | 152 |
| pig/sus | AAATTACCATAACATCACT | 146 | 16S ribosomal RNA gene | AJ002189.1 | pig_f | CCGAGTGATTTTAATCTAGACAA | 153 |
| | | | | | pig_b | AACTTGTTCCGTTGATCAAAATT | 154 |
| Cow/bovine | TCACTCTATCGCTCATTGA | 147 | 16S ribosomal RNA gene | AY526085.1 | bovine_f | GAGCGATTTTAAAGACTAGACCC | 155 |
| | | | | | bovine_b | TAACTTGTTCCGTTGATCAAGTT | 156 |
| SV40 TAg | CTCAACATTCTACTCCTCC | 122 | T-antigen | J02400.1 | SV40 Tag_f | AACCTGTTTTGCTCAGAAGAAATGC | 47 |
| | | | | | SV40 Tag_b | GAAGGAAAGTCCTTGGGGTCTTCTA | 48 |
| SV40 VP1 | ACCACAGTGCTTCTTGAT | 123 | VP1 | J02400.1 | SV40 VP1_f | GAACCTACACAGGTGGGGAAAATGT | 45 |
| | | | | | SV40 VP1_b | CAAGGGCCCAACACCCTGCTCAT | 46 |
| SV40 VP3 | CCCTGGACAACTTCCTTT | 124 | VP3 | J02400.1 | SV40 VP3_f_bio | AAGCTTATGAAGATGGCCCCAACA | 49 |
| | | | | | SV40_VP3_b | ATTCCTCCTTTTATGACGAGCTTTG | 50 |
| Y-chromosome, mouse | ACCAACAGCAGCAGCAGTT | 125 | sex determining region of Chr Y (Sry) | NM_011564.1 | Y_mouse_f | TCCATGACCACCACCAGCAGAAGCA | 43 |
| | | | | | Y_mouse_b | CTGGGGGTGGTCATGGAACTGAT | 44 |
| Y-chromosome, human/monkey | CAGCTAGGCCACTTACCGC | 126 | sex determining region of Chr Y (Sry) | NM_003140.1 | Y_hum/mon_f | GTACGAAAGCCACACACTCAAGAA | 39 |
| | | | | | Y_hum/mon_b | TTGTCCTACAGCTTTGTCCAGTGG | 40 |
| Y-chromosome, rat | AGAAGGGCTTACTACATAC | 127 | sex determining region of Chr Y (Sry) | AF274872.1 | Y_rat_f | GGAGGAGACCAAAATGTGTGTAAGG | 41 |
| | | | | | Y_rat_b | CATCGATTAAATGCCATAAGAATGC | 42 |
| HSV1 (HHV1) | TGTTCACCACGAGTACCTG | 128 | UL42 | NC_001806.1 | HSV1_f | ACGAGGCCGCAGCTCACCAAGGT | 23 |
| | | | | | HSV1_b | CGCCCTCCTCGCGGGCAGCAAA | 24 |

TABLE 1-continued

Probes polynucleotides and oligonucleotides (primer) overview

| Target (contaminating organism)/ Probe name | Probe oligonucleotide sequence 5' to 3' | Probe SEQ ID NO: | Region | Accession number | Primer name (F, forward; b, backward) | Primer sequence 5' to 3' | Primer SEQ ID NO: |
| --- | --- | --- | --- | --- | --- | --- | --- |
| HSV2 (HHV2) | TGTTTAACGCGCGCACCTG | 129 | UL42 | NC_001798.1 | HSV2_f | ACGAAGCCCCAGCTCACG AAGGT | 25 |
| | | | | | HSV2_b | CGCCCTCCTCGCGGGCGG CAAA | 26 |
| VZV (HHV3) | TGCACGGGTGCGGAACGTT | 130 | orthologue of HHV-1 UL42 | NC_001348.1 | VZV_f | CATCCTTCACAGATTCCA TGTTCG | 27 |
| | | | | | VZV_b | TCCCCCATGGTTGGATTG TATATC | 28 |
| EBV (HHV4) | AGATAAAAGTCCCCGGGTG | 145 | UL42 family | NC_009334.1 | EBV_f | TTATTTAACCACGCCTCC GAAGAG | 29 |
| | | | | | EBV_b | TGAAGGAGATGGACTGAC CGTATG | 30 |
| CMV (HHV5) | ACAGACCGTTGCGGCTGGC | 131 | orthologue of HHV-1 UL42 | NC_006273.1 | CMV_f | GTTCCCGACGTAATTTTT GTCGAA | 31 |
| | | | | | CMV_b | GCACGTTGCGTATAGTTA CGGAGC | 32 |
| HHV6 | GCACTTCCGTCGTCGTTCT | 132 | Pp41 | NC_001664.1 | HHV6_f | AAATAAGCTAGAGCCCGC AGTTCC | 33 |
| | | | | | HHV6_b | ACGAATGGGTAAACAAGA TGACGG | 34 |
| HHV7 | GCCAACGTCATTTCATTTT | 133 | UL42 | NC_001716.1 | HHV7_f | TGAAACACAACTTTCCCG CTATGA | 35 |
| | | | | | HHV7_b | CGGTCACAAAGAACAAAC GCAGTA | 36 |
| HHV8 | ATGTCACGATCGACAGCGT | 134 | UL42 | NC_009333.1 | HHV8_f | GACTTCTTCCCCTTCAGA CCATCC | 37 |
| | | | | | HHV8_b | AAACAAAAGAGGACCAAA CGGTGA | 38 |
| HIV1_M,N | ATCTATAAAAGATGGATAATC C | 135 | Gag | AF004885.1 | HIV1_gag_f | GGAAGTGAYATAGCWGGA ACTACYAG | 67 |
| | | | | | HIV1_gag_b | ACAGGGCTATACATTCTT ACTAT | 68 |
| HIV1_M | CTGTCATGGGTACCAGCACAC AA | 136 | Pol | AF004885.1 | HIVI_M, O_pol_f | ATAGTRACAGAYTCACAR TATGCA | 69 |
| HIV1_O | CTTACATGGGTTCCTGCCCA | 137 | Pol | L20587.1 | | | |
| HIV1_N | CTCTCTTGGGTACCTGCACA | 138 | Pol | AJ006022.1 | HIV1_N_pol_f | ATAGTCACTGACTCTCAG TATGCT | 70 |
| | | | | | HIV1_M,N, O_pol_b | ATTTATCTACTTGTTCAT TTCCTCC | 71 |
| HIV1_N | GTTGCTATTATGTCTAT | 139 | Gag | AJ006022.1 | HIV1_O/N_gag_f_bio | GGGATTGGGGGGTACAC TGCAGG | 72 |
| HIV1_O | GATGCTAATATGTCTAT | 140 | Gag | L20587.1 | HIV1_O/N_gag_b | CTGCTGTCTCTGTAATA RACCCGAA | 73 |
| HIV2 | AAGAAATACAATTCCTCCA | 141 | Pol | AY509259.1 | HIV2/SIV_pol_f | GAAGGGGAGGAATAGGG GATATGAC | 74 |
| SIV | AAGAAATACAATTTCAACA | 142 | Pol | M83293.1 | HIV2/SIV_pol_b | TCTGCCTTCTCTGWAAT AGACCCG | 75 |
| HIV2_2A/SIV | GTGGTCAAGAGACAACA | 143 | Env | AY509259.1/ M83293.1 | HIV2/SIV_env_f | ACGTTGTCGGCTCAGTC YCGGACTTTA | 76 |
| HIV2_2U/B | GTGGTCAAAAGACAACA | 144 | Env | AY530889.1/ U27200.1 | HIV2/SIV_env_b | GTCCCCAGACGGTCAG YCGCAACA | 77 |

Example 2

Extraction of DNA from Cell Culture

DNA was extracted from various cell cultures possibly infected with *Mycoplasma, A. laidlawii* or SMRV. An amount of 1 ml of cell suspensions, containing $10^5$ to $10^6$ cells, was transferred to a microcentrifuge tube and collected by centrifugation at 2600 rpm, 5 min in a tabletop centrifuge. The pellet was resuspended in PBS. The mixture was incubated for 15 minutes at 95° C. Subsequently, cell debris was pelleted and the supernatant was transferred into new microcentrifuge tubes and stored at −20° C.

Importantly, for *Mycoplasma* testing alone, 1 to 2 µl of cell culture medium could also be used.

Example 3

Development of the Multiplex Cell Culture Contamination PCR

Oligonucleotide primers that met requirements of Example 1 were used for subsequent amplification of cloned DNA or DNA extracted as mentioned above. One primer of each pair was biotinylated at the 5' terminus for labelling the target strand of the amplified product. The different target genes were amplified in a single multiplex PCR. For initial validation of primers, singleplex PCR, for each individual primer pair, were performed under same conditions. The 50 µl reactions comprised 1× QIAGEN Multiplex PCR Master Mix (containing 3 mM $MgCl_2$, dNTP mix, 0.5× Q-solution and HotStarTaq DNA polymerase), 0.2 µM each primer, and 1-2 µL of template DNA. Using a Mastercycler (Eppendorf, Germany) PCR products were amplified by incubation at 95° C. for 15 minutes to activate the enzyme, followed by 40 cycles of denaturation at 94° C. for 30 seconds, annealing at 61° C. for 90 seconds, and extension at 72° C. for 60 seconds. Final extension was performed at 72° C. for 10 minutes and reactions were stored at 4° C.

Example 4

Coupling of Oligonucleotide Probes

The sequences of 5' amino-modified C-12-linked oligonucleotide probes (purchased from MWG-Biotech) are shown in Table 1. Probes were coupled to carboxylated beads by a carbodiimide-based coupling procedure. For each combination of probe and bead set, 2.5 million carboxylated beads (xMAP; Luminex Corp., Austin, Tex.) were suspended in 25 µl of 0.1 M 2-(N-morpholino)ethanesulfonic acid, pH 4.5 (MES). Probe oligonucleotides (400 pmol) and 200 µg of N-(3-dimethylaminopropyl)-N-ethylcarbodiimide (EDC) were added and thoroughly mixed with the beads. Incubation was performed in the dark under agitation for 30 min and was interrupted by a thorough mixing step after 15 min. The addition of EDC and incubation steps were repeated and the coupled beads were finally washed once with 0.5 ml of 0.2 g/liter Tween-20 and once with 0.5 ml of 1.0 g/liter sodium dodecyl sulfate before being stored in 100 µl of TE buffer at 4° C. in the dark. Coupling efficiency of new bead batches compared to old ones was verified by hybridization to 1.0 to 4.0 µl of biotinylated PCR product of the respective target. New coupling batches showing a coefficient of variation (CV) below 15% were used for further analyses (data not shown).

Example 5

Development of Multiplex Cell Culture Contamination Hybridisation Method

Multiplex PCR products were denatured and hybridized to bead-coupled target-specific oligonucleotide probes in 96-well plates, allowing PCR products from 96 individual cell cultures to be processed in parallel. After transfer into wash plates with filter bottoms, unhybridized DNA was removed. Subsequently, biotinylated PCR products were stained by Strep-PE conjugate. After further washing steps, beads were analyzed in the Luminex reader, which contains two lasers to identify the bead set by the internal bead color and to quantify the reporter fluorescence on the bead.

Following multiplex PCR amplification, 10 µl of each reaction mixture were transferred to 96-well plates containing 33 µl of tetramethylammonium chloride (TMAC) hybridization solution (0.15 M TMAC, 75 mM Tris-HCl, 6 mM EDTA, 1.5 g/liter Sarkosyl, pH 8.0), 7.0 µl of 1×TE, 0.2 to 1.2 µM of each antisense oligonucleotide (Seq ID NR. 157 to 165) and a mixture of 2,000 probe-coupled beads of each set. Antisense oligonucleotides were used to suppress hybridization of some primers to probes. The mixture was heated to 95° C. for 10 min in a laboratory oven, immediately placed on ice for 1 min, and then transferred to a thermomixer. Hybridization was performed at 41° C. for 30 min under agitation. The samples were transferred to a 96-well wash plate (Millipore, Bedford, Mass.), pre-equilibrated with washing buffer (phosphate-buffered saline, 0.02% Tween). Subsequently, the beads were washed once with 100 µl of washing buffer on a vacuum wash station (Millipore). On a horizontal shaker at room temperature, beads were resuspended for 20 min in 50 µl of streptavidin-R-phycoerythrin (Strep-PE; Molecular Probes, Eugene, Oreg.) diluted 1:1,600 in 2.0 M TMAC, 75 mM Tris-HCl, 6 mM EDTA, 1.5 g/liter Sarkosyl, pH 8.0. Beads were then washed three times with 100 µl washing buffer and finally resuspended in 100 µl washing buffer for 5 min on a shaker. Beads were analyzed for internal bead color and R-phycoerythrin reporter fluorescence on a Luminex 100 analyzer. The median reporter fluorescence intensity (MFI) of at least 100 beads was computed for each bead set in the sample.

In order to determine the specificity of the hybridisation, target-specific probes were coupled individually to defined bead sets and hybridized to 10 µl (100 to 300 ng DNA) of PCR products derived from single- and multiplex PCRs on crudely purified DNA from cell cultures (different species, cell lines with markers) or highly purified plasmid DNAs (SMRV, SV40). Detection of all targets was highly specific and no cross-hybridisation was observed even for highly related target genes, such as the 16S ribosomal RNA gene that was used for the detection of different species. More importantly, the SMRV detection by gag and env probes was not affected by endogenous retroviruses or HIV.

Example 6

Determination of the Detection Limit of SMRV, HPV-18 (HeLa), Human Beta Globin and PolA Analytic sensitivity of multiplex PCR, containing specific primers for gag and env of SMRV, was determined for plasmid clone SMRV (ATCC Nr. 45034). The plasmid preparation was quantified using NanoDrop® ND-1000 (NanoDrop Technologies, Wilmington, Del., USA). The copy numbers was determined on the basis of the molecular weight of the plasmid. 10-fold endpoint dilution series were prepared in 100 ng/μL of human placenta (HP-) DNA in a total volume of 30 μL. Two to three replicates were assayed independently by the multiplex PCR and subsequent hybridisation to the multiplex hybridisation mixture, containing also gag and env specific oligonucleotide probes. Despite the co-amplification and co-detection of human beta-globin and PolA, both probes detected as little as 10 copies of SMRV. Using 100 μL of HP-DNA alone, no SMRV signal was detected showing a high specificity of the SMRV detection. Thus, presence of other human endogenous retroviruses does not cause false-positives.

Next, we aimed at determining the sensitivity of the multiplex PCR for the detection of HPV-18 positive HeLa cells. DNA extracts of $10^6$ HeLa cells were prepared as described in Example 2, followed by a 10-fold dilution series in water. After multiplex PCR and detection with the multiplex hybridisation mixture, including the HPV-18 type-specific oligonucleotide probe, less than 5 HeLa genome equivalents were specifically detected. The co-amplification and co-detection of human beta-globin and PolA resulted in detection limits of less than 5 and less than 50 genome equivalents, respectively.

Example 7

Determination of the Detection Limits for the Simultaneous Detection of Various Contaminations in Cell Cultures We aimed at determining the sensitivity of the multiplex PCR for the simultaneous detection of multiple contaminations present in the same sample. To this end we mixed $10^6$ cells of 10 different cell lines (Table 2, 1 to 10) and conducted a combined 3-fold dilution series in $10^6$ human (11) and mouse background cells (12). DNA extracts of cell mixtures were prepared as described in Example 2. The Multiplex PCR was performed as described in Example 3 with primers indicated in Table 1 (SEQ ID 1 to 66, 149-152). Each cell line (1 to 10) was titrated down from 300 to 0.01 cells in 6,000 background cells per PCR reaction. Subsequently, PCR products were simultaneously detected using specific oligonucleotide probes coupled to Luminex beads (Table 1, SEQ ID 78 to 134, 145 and 148). Despite the presence of 70 primers in a single PCR reaction and simultaneous co-amplification of 16 PCR products, the multiplex PCR with subsequent Luminex analysis used for the detection of cell culture contaminations proved to be very sensitive. As such, the detection limit for detecting "contaminating" HeLa cells was below 3 (<0.1%) cells in a background of 6,000 cells of the parent cell line. Less than 1 contaminating cell (<0.1%) among 6,000 cells was sufficient to detect cross-species contaminations (Table 3).

TABLE 2

Overview cell lines used for example 7

| | Cell line | Species | Sex | Infection/Contamination |
|---|---|---|---|---|
| 1 | HeLa | Human | female | HPV18 |
| 2 | HEK 293T | Human | female | Adenovirus 5, SV40 |
| 3 | Namalwa | Human | female | EBV |
| 4 | SW480 | Human | male | |
| 5 | CHO | Chinese Hamster | female | |
| 6 | MDCK II | Canine | unknown | |
| 7 | NIH3T3 | Mouse | female | |
| 8 | Ratte a-tag R4 | Rat/Mouse hybrid | female | |
| 9 | Alexander | Human | female | HBV |
| 10 | CEM | Human | female | M. fermentans |
| 11 | BJA-B | Human | female | M. hyorhinis, M. arginini |
| 12 | Sp2/0-Ag8 | Mouse | female | |

TABLE 3

Detection limits for markers of contaminating cell lines

| cell line (marker) | DL for contaminating cells in a background of 6,000 cells/PCR | |
|---|---|---|
| | cell # | % |
| HEK 293T (SV40 TAg) | <10 | <0.2 |
| HEK 293T (SV40 VP1) | <10 | <0.2 |
| HEK 293T (Adenovirus 5) | <3 | <0.06 |
| HeLa (HPV18) | <3 | <0.06 |
| Namalva (EBV) | <100 | <2.0 |
| Alexander (HBV) | <1 | <0.02 |
| CEM (human) | <1 | <0.02 |
| NIH3T3 (mouse) | <1 | <0.02 |
| a-tag R4 (rat) | <1 | <0.02 |
| CHO (chinese hamster) | <1 | <0.02 |
| MDCK II (canine) | <1 | <0.02 |
| SW480 (human Y-chromosome) | <100 | <2.0 |

Example 8

Commercial tests for the detection of *Mycoplasma* are widely used. One of the most frequently used in Germany is the Venor®GeM from Minerva Biolabs that can detect between 2 and 5 copies of *Mycoplasma* upon PCR and gel electrophoresis but cannot genotype the respective species.

In order to validate the novel multiplex PCR to this well-validated *Mycoplasma* test, we performed six-fold dilution series of a *Mycoplasma* positive cell lysate in a *Mycoplasma* negative cell lysate (each with $10^6$ human genome equivalents per 100 μL of lysate) used 2 μL of the mixture for PCR. The Venor®GeM kit for conventional PCR was performed according to the manufacturer's instructions using the AmpliTaq Gold polymerase, AmpliTaq gold buffer and 2.5 mM $MgCl_2$ (Applied Biosystems, Branchburg, N.J., USA). Briefly, 2 μL of DNA extracts were amplified in 25 μL containing 1× AmpliTaq Gold buffer, 2.5 μL of the primer/dNTP mix, 2.5 mM $MgCl_2$, 2.5 μL of the internal control DNA and 1 U of DNA AmpliTaq Gold polymerase. A 15 min denaturation step at 94° C. was followed by 39 cycles of amplification with a Mastercycler (Eppendorf, Germany). Each cycle included a denaturation step at 94° C. for 30 s, an annealing step at 55° C. for 30 s, and an elongation step at 72° C. for 30 s. The experiment was performed with positive and several water PCR controls. For final analysis, 5 μL of PCR products were loaded on a 1.5% agarose gel.

The Multiplex PCR was performed as described in Example 3 with all primers indicated in Table 1 (SEQ ID 1 to 66). Subsequently, PCR products were simultaneously detected using specific oligonucleotide probes coupled to Luminex beads (Table 1, SEQ ID 78 to 120, 122 to 134, 145).

Upon gel electrophoresis, the Venor®GeM kit allowed the detection of the *Mycoplasma* genus in up to 1.300-fold diluted DNA extracts, while the internal PCR control was positive for all reactions. The multiplex PCR assay with subsequent Luminex detection showed a six-fold increased sensitivity allowing the detection and typing of *Mycoplasma* in 7.800-fold diluted DNA extracts. More remarkably, this increased sensitivity was observed despite the co-detection of POLA, human β-globin, human Y-chromosome, adenoviral and EBV DNA that was present in the DNA extract.

Example 9

Evaluation of the Cell Culture Contamination Multiplex PCR with Cell Culture Samples A broad spectrum of cell lines was obtained from 12 individual laboratories within the German Cancer Research Center (DKFZ). DNA extracts of $10^6$ cells from 59 cell lines were prepared as described in Example 2. The multiplex primer mixture comprised all primers listed in Table 1 (SEQ ID 1 to 66) and subsequent detection was performed using the oligonucleotide probes shown in Table 1 (SEQ ID 78 to 120, 122 to 134, 145). Of all cell lines, 19 (32%) were *Mycoplasma* positive with *M. hyorhinis* being most prevalent (73% of positive cell lines). Of three HPV-18 positive cell lines, one was derived from a cervical carcinoma being naturally infected with HPV-18. For the remaining two cell lines (SiHa, and CEM), the presence of HPV-18 suggested a HeLa contamination. SMRV was found positive with both gag and env probes in 8 cases (13%). However, 4 of these cases were found in different preparations of the same Namalwa cell line. In addition, two mouse cell lines were found to be cross-contaminated with human cells as it was demonstrated by positive signals with the human- and mouse-specific beta-globin oligonucleotide probes. Moreover, as confirmed by POLA, species-specific beta globin or mitochondrial DNA detection, none of the 59 PCRs failed.

Example 10

Simultaneous Detection of all Targets by McCT

To determine the ability of McCT to detect multiple targets at the same time, an artificial mixture was generated from several positive controls. In total, 34 different lysates and positive controls were mixed to obtain a sample positive for all PCR targets. For pig DNA and some *Mycoplasma* species no suitable control DNA was available.

The Multiplex PCR was performed as described in Example 3 with all primers indicated in Table 1 (SEQ ID 1 to 66 and 149 to 154). Subsequently, PCR products were simultaneously detected using specific oligonucleotide probes coupled to Luminex beads (SEQ ID: 78 to 119, and 121 to 134, and 145, 146, 148). The assay was performed for all 34 controls and the artificial mixture. For each probe, MFI values in reactions with no PCR product added to the hybridization mixture (water control) were considered background values. The cutoff was defined as 1.2 times the water control value plus 5 MFI.

Despite the fact that some targets were diluted 34-fold, 41 of 42 present "contaminations" could be detected simultaneously as determined in duplicates (Table. 4). VZV was positive only once in one replicate. This data highlights the good suitability and robustness of McCT to detect more than 40 targets simultaneously.

TABLE 4

Simultaneous detection of multiple contaminations

| | | Target-specific bead-coupled oligonucleotides | | | | | | | | | | | | | | |
|---|---|---|---|---|---|---|---|---|---|---|---|---|---|---|---|---|
| | | Internal positive control | human β-globin | human β-globin | mouse β-globin | mouse DNA | rat β-globin | rat DNA | monkey β-globin | green monkey DNA | chinese hamster DNA | canine DNA | feline DNA | guinea pig | rabbit DNA | pig DNA | Y chromosome human/monkey | Y chromosome mouse |
| DNA target | A. laidlawii | 75.5[a] | 503 | 177 | 8 | 5 | 7 | 4 | 7 | 6 | 5 | 5 | 5 | 35 | 7 | 3 | 561 | 3 |
| | Adenovirus | 42 | 244 | 72 | 18 | 7 | 10 | 4 | 10 | 7 | 6 | 8 | 7 | 31 | 9 | 8 | 11 | 5 |
| | Cat | 38 | 7 | 10 | 12 | 6 | 7 | 3 | 7 | 5 | 4 | 7 | 501 | 25 | 7 | 4 | 10 | 2 |
| | Chinese hamster | 61 | 9 | 11 | 10 | 7 | 8 | 5 | 9 | 7 | 284 | 7 | 6 | 35 | 8 | 5 | 11 | 4 |
| | CMV | 99 | 266 | 60 | 5 | 4 | 6 | 5 | 6 | 4 | 3 | 3 | 3 | 36 | 4 | 2 | 482 | 2 |
| | Dog | 38 | 10 | 13 | 11 | 11 | 10 | 1 | 9 | 8 | 6 | 402 | 9 | 22 | 10 | 8 | 13 | 5 |
| | EBV | 44 | 244 | 75 | 10 | 5 | 8 | 7 | 8 | 5 | 5 | 6 | 6 | 34 | 7 | 4 | 10 | 3 |
| | Green-monkey | 115 | 339 | 21 | 7 | 4 | 6 | 4 | 6 | 387 | 3 | 5 | 5 | 18 | 5 | 2 | 9 | 2 |
| | Guinea pig | 114 | 5 | 6 | 5 | 4 | 5 | 1 | 8 | 3 | 4 | 4 | 4 | 501 | 4 | 2 | 9 | 1 |
| | HBV | 61 | 7 | 9 | 7 | 1052 | 7 | 2 | 377 | 5 | 4 | 5 | 4 | 40 | 6 | 3 | 9 | 5 |
| | HEK293T | 41 | 212 | 73 | 74 | 7 | 9 | 3 | 6 | 5 | 4 | 5 | 7 | 32 | 10 | 7 | 12 | 2 |
| | HHV 1 | 55 | 5 | 7 | 13 | 4 | 6 | 6 | 13 | 8 | 6 | 7 | 4 | 26 | 4 | 2 | 9 | 3 |
| | HHV 2 | 52 | 7 | 8 | 5 | 5 | 7 | 2 | 10 | 3 | 4 | 3 | 5 | 27 | 6 | 3 | 10 | 2 |
| | HHV 6 | 257 | 273 | 103 | 6 | 10 | 6 | 3 | 7 | 5 | 4 | 4 | 4 | 21 | 4 | 2 | 792 | 2 |
| | HHV 7 | 80 | 313 | 109 | 5 | 3 | 7 | 1 | 6 | 4 | 4 | 3 | 3 | 26 | 4 | 3 | 8 | 3 |
| | HHV 8 | 2 | 6 | 8 | 6 | 4 | 9 | 3 | 6 | 6 | 3 | 4 | 4 | 31 | 5 | 2 | 8 | 2 |
| | HPV18 | 35 | 168 | 65 | 11 | 7 | 6 | 4 | 8 | 6 | 5 | 5 | 6 | 24 | 8 | 5 | 12 | 4 |
| | M. arginini/hominis | 164 | 261 | 119 | 7 | 4 | 6 | 1 | 7 | 4 | 4 | 7 | 5 | 18 | 5 | 2 | 9 | 2 |
| | M. fermentans | 39 | 272 | 98 | 5 | 3 | 5 | 2 | 5 | 3 | 3 | 4 | 3 | 29 | 4 | 3 | 7 | 2 |
| | M. orale | 54 | 409 | 113 | 9 | 6 | 7 | 1 | 7 | 5 | 4 | 5 | 4 | 29 | 7 | 4 | 11 | 3 |
| | M. synoviae | 71 | 7 | 11 | 8 | 6 | 8 | 18 | 8 | 6 | 5 | 5 | 638 | 25 | 8 | 4 | 10 | 4 |
| | M. hyorhinis | 60 | 335 | 92 | 4 | 4 | 6 | 4 | 5 | 3 | 3 | 8 | 4 | 16 | 4 | 5 | 7 | 1 |
| | M. pneumoniae | 1 | 5 | 7 | 5 | 3 | 5 | 1 | 5 | 4 | 3 | 4 | 3 | 29 | 4 | 2 | 7 | 2 |
| | Mouse | 58 | 6 | 8 | 69 | 908 | 6 | 3 | 8 | 5 | 4 | 5 | 4 | 34 | 6 | 3 | 9 | 2 |
| | Rabbit | 76 | 5 | 7 | 5 | 3 | 5 | 2 | 5 | 3 | 5 | 4 | 4 | 53 | 110 | 2 | 8 | 2 |
| | Rat | 38 | 6 | 8 | 8 | 4 | 503 | 52 | 6 | 4 | 4 | 4 | 4 | 27 | 11 | 2 | 8 | 3 |
| | SMRV | 57 | 336 | 99 | 8 | 5 | 7 | 4 | 8 | 6 | 4 | 5 | 5 | 34 | 8 | 4 | 11 | 3 |
| | Sry hum/monk | 103 | 348 | 107 | 8 | 133 | 9 | 3 | 8 | 5 | 102 | 6 | 5 | 31 | 7 | 6 | 795 | 3 |
| | SV40 Tag | 56 | 258 | 110 | 9 | 6 | 8 | 5 | 9 | 7 | 5 | 6 | 5 | 23 | 8 | 5 | 11 | 4 |
| | SV40 VP1 | 47 | 217 | 71 | 12 | 6 | 8 | 3 | 9 | 5 | 5 | 6 | 6 | 27 | 9 | 6 | 10 | 4 |
| | SV40 VP3 | 82 | 387 | 112 | 10 | 6 | 8 | 5 | 8 | 3 | 5 | 6 | 6 | 37 | 8 | 4 | 11 | 4 |
| | VZV | 1 | 6 | 6 | 4 | 4 | 6 | 1 | 5 | 7 | 3 | 4 | 4 | 16 | 4 | 2 | 7 | 1 |
| | Y-chromosome mouse | 66 | 8 | 11 | 77 | 886 | 8 | 4 | 7 | 3 | 5 | 6 | 5 | 37 | 8 | 5 | 11 | 21 |
| | Mixture | 55 | 549 | 205 | 194 | 528 | 370 | 112 | 23 | 52 | 47 | 106 | 372 | 272 | 15 | 8 | 755 | 28 |
| | Mixture | 40 | 414 | 162 | 135 | 375 | 287 | 81 | 23 | 34 | 29 | 72 | 261 | 184 | 17 | 7 | 634 | 20 |
| | H₂O control | 1 | 5 | 7 | 7 | 6 | 6 | 1 | 8 | 4 | 3 | 4 | 3 | 32 | 6 | 3 | 8 | 2 |
| | cutoff | 6 | 11 | 13 | 13 | 12 | 12 | 6 | 15 | 10 | 9 | 10 | 9 | 43 | 12 | 9 | 15 | 7 |

TABLE 4-continued

Simultaneous detection of multiple contaminations

Target-specific bead-coupled oligonucleotides

| | | HeLa | SMRV env | SMRV gag | SV40 VP3 | SV40 TAG | SV40 VP1 | Adeno-virus | Adeno-virus 5 | HSV1 | HSV2 | VZV | EBV | CMV | HHV6 | HHV7 | HHV8 | HBV ace | HBV abd | HBV fgh | Mycoplasma universal 1 |
|---|---|---|---|---|---|---|---|---|---|---|---|---|---|---|---|---|---|---|---|---|---|
| DNA target | A. laidlawii | 24 | 4 | 3 | 5 | 3 | 6 | 3 | 3 | 18 | 18 | 19 | 18 | 19 | 16 | 21 | 24 | 9 | 7 | 9 | 10 |
| | Adenovirus | 26 | 6 | 5 | 8 | 5 | 7 | 1497 | 3 | 21 | 22 | 21 | 19 | 20 | 17 | 25 | 25 | 11 | 11 | 11 | 9 |
| | Cat | 24 | 5 | 3 | 5 | 4 | 5 | 2 | 118 | 19 | 18 | 19 | 18 | 18 | 15 | 21 | 24 | 10 | 9 | 8 | 4 |
| | Chinese hamster | 26 | 6 | 4 | 7 | 6 | 8 | 4 | 3 | 20 | 22 | 19 | 19 | 21 | 18 | 23 | 24 | 9 | 11 | 9 | 7 |
| | CMV | 21 | 2 | 1 | 3 | 1 | 2 | 1 | 1 | 17 | 17 | 16 | 15 | 149 | 13 | 18 | 22 | 6 | 5 | 7 | 65 |
| | Dog | 27 | 8 | 6 | 7 | 7 | 8 | 5 | 4 | 22 | 23 | 21 | 19 | 20 | 20 | 23 | 27 | 9 | 9 | 8 | 6 |
| | EBV | 24 | 4 | 3 | 5 | 4 | 7 | 3 | 3 | 19 | 19 | 18 | 335 | 18 | 16 | 22 | 24 | 8 | 9 | 9 | 6 |
| | Green-monkey | 23 | 3 | 3 | 8 | 3 | 6 | 3 | 1 | 18 | 19 | 19 | 15 | 17 | 14 | 19 | 23 | 8 | 8 | 7 | 6 |
| | Guinea pig | 22 | 2 | 2 | 4 | 1 | 3 | 2 | 1 | 17 | 17 | 16 | 16 | 15 | 14 | 22 | 23 | 6 | 6 | 7 | 3 |
| | HBV | 23 | 5 | 5 | 6 | 43 | 5 | 1 | 2 | 19 | 18 | 19 | 17 | 18 | 15 | 21 | 23 | 520 | 363 | 246 | 6 |
| | HEK293T | 26 | 7 | 2 | 7 | 402 | 2 | 1415 | 127 | 22 | 22 | 20 | 20 | 21 | 19 | 23 | 26 | 9 | 9 | 8 | 6 |
| | HHV 1 | 22 | 2 | 5 | 4 | 410 | 153 | 1 | 1 | 918 | 17 | 15 | 15 | 15 | 14 | 20 | 22 | 6 | 6 | 7 | 3 |
| | HHV 2 | 23 | 4 | 3 | 5 | 3 | 4 | 2 | 2 | 19 | 193 | 18 | 15 | 16 | 15 | 21 | 23 | 8 | 7 | 8 | 102 |
| | HHV 6 | 22 | 2 | 2 | 3 | 4 | 2 | 1 | 2 | 17 | 17 | 16 | 14 | 15 | 761 | 19 | 22 | 6 | 6 | 7 | 3 |
| | HHV 7 | 23 | 2 | 2 | 4 | 1 | 2 | 1 | 1 | 18 | 17 | 16 | 16 | 15 | 13 | 727 | 22 | 8 | 6 | 7 | 4 |
| | HHV 8 | 22 | 2 | 2 | 4 | 2 | 2 | 1 | 1 | 18 | 18 | 17 | 15 | 15 | 14 | 23 | 357 | 5 | 6 | 7 | 4 |
| | HPV18 | 165 | 5 | 4 | 8 | 5 | 7 | 4 | 3 | 20 | 19 | 19 | 19 | 20 | 18 | 22 | 25 | 11 | 8 | 9 | 5 |
| | M. arginini/hominis | 23 | 3 | 3 | 8 | 3 | 3 | 2 | 1 | 18 | 19 | 19 | 16 | 17 | 14 | 19 | 23 | 8 | 8 | 7 | 29 |
| | M. fermentans | 22 | 3 | 2 | 8 | 1 | 2 | 2 | 3 | 19 | 18 | 16 | 16 | 15 | 14 | 18 | 24 | 5 | 6 | 7 | 73 |
| | M. orale | 24 | 4 | 4 | 5 | 4 | 7 | 3 | 1 | 19 | 19 | 18 | 16 | 17 | 15 | 21 | 24 | 9 | 8 | 8 | 21 |
| | M. synoviae | 26 | 5 | 3 | 7 | 211 | 200 | 4 | 3 | 19 | 20 | 19 | 18 | 19 | 17 | 22 | 25 | 11 | 11 | 9 | 152 |
| | M. hyorhinis | 270 | 2 | 2 | 5 | 1 | 1 | 1 | 1 | 17 | 18 | 16 | 16 | 14 | 16 | 21 | 24 | 9 | 7 | 8 | 6 |
| | M. pneumoniae | 22 | 2 | 2 | 8 | 1 | 2 | 2 | 2 | 18 | 18 | 18 | 16 | 15 | 14 | 18 | 24 | 5 | 6 | 6 | 5 |
| | Mouse | 22 | 3 | 3 | 5 | 3 | 5 | 3 | 1 | 18 | 19 | 17 | 16 | 17 | 14 | 20 | 23 | 7 | 7 | 8 | 5 |
| | Rabbit | 22 | 2 | 2 | 7 | 4 | 1 | 1 | 1 | 19 | 19 | 18 | 16 | 14 | 14 | 20 | 23 | 6 | 6 | 8 | 3 |
| | Rat | 23 | 3 | 2 | 64 | 1 | 1 | 1 | 2 | 18 | 18 | 17 | 16 | 15 | 14 | 20 | 23 | 7 | 7 | 7 | 4 |
| | SMRV | 74 | 1425 | 686 | 5 | 2 | 4 | 4 | 3 | 20 | 19 | 19 | 18 | 19 | 17 | 22 | 24 | 9 | 9 | 8 | 6 |
| | Sry hum/monk | 25 | 4 | 2 | 7 | 4 | 7 | 3 | 3 | 19 | 18 | 18 | 18 | 17 | 16 | 21 | 24 | 9 | 8 | 7 | 6 |
| | SV40 Tag | 25 | 6 | 4 | 4 | 3 | 6 | 5 | 4 | 20 | 20 | 21 | 18 | 19 | 18 | 22 | 24 | 12 | 10 | 10 | 5 |
| | SV40 VP1 | 26 | 5 | 5 | 7 | 301 | 150 | 4 | 4 | 20 | 20 | 19 | 20 | 20 | 18 | 22 | 25 | 11 | 11 | 10 | 6 |
| | SV40 VP3 | 25 | 5 | 4 | 6 | 45 | 7 | 4 | 3 | 19 | 17 | 17 | 17 | 19 | 17 | 22 | 26 | 10 | 10 | 9 | 6 |
| | VZV | 23 | 2 | 2 | 5 | 4 | 1 | 3 | 1 | 17 | 17 | 114 | 15 | 15 | 14 | 19 | 23 | 6 | 6 | 6 | 2 |
| | Y-chromosome mouse | 24 | 5 | 4 | 5 | 5 | 8 | 4 | 4 | 19 | 20 | 19 | 19 | 19 | 17 | 22 | 25 | 8 | 7 | 9 | 6 |
| | Mixture | 302 | 622 | 242 | 11 | 301 | 350 | 797 | 50 | 835 | 88 | 26 | 247 | 106 | 848 | 245 | 313 | 35 | 13 | 16 | 437 |
| | Mixture | 231 | 446 | 179 | 12 | 215 | 195 | 552 | 35 | 645 | 61 | 18 | 148 | 79 | 754 | 209 | 251 | 35 | 15 | 16 | 353 |
| | H₂O control | 22 | 5 | 4 | 4 | 5 | 5 | 1 | 1 | 17 | 17 | 15 | 15 | 15 | 13 | 18 | 22 | 6 | 6 | 7 | 5 |
| | cutoff | 31 | 11 | 10 | 10 | 11 | 11 | 6 | 6 | 25 | 25 | 23 | 23 | 23 | 21 | 27 | 31 | 12 | 12 | 13 | 11 |

TABLE 4-continued

Simultaneous detection of multiple contaminations

Target-specific bead-coupled oligonucleotides

| | | Mycoplasma universal 2 | M. gallisepticum | M. pneumoniae | M. fermentans | M. hyorhinis | M. hominis | M. arginini | M. pirum | M. synoviae | M. orale | M. salivarium | Acholeplasma laidlawii | A. granularum |
|---|---|---|---|---|---|---|---|---|---|---|---|---|---|---|
| DNA target | A. laidlawii | 3 | 3 | 4 | 3 | 4 | 5 | 5 | 4 | 4 | 4 | 4 | 108 | 5 |
| | Adenovirus | 6 | 4 | 7 | 5 | 6 | 6 | 5 | 6 | 6 | 6 | 6 | 11 | 9 |
| | Cat | 3 | 3 | 4 | 3 | 4 | 4 | 4 | 5 | 4 | 5 | 4 | 9 | 5 |
| | Chinese hamster | 4 | 2 | 5 | 4 | 4 | 5 | 6 | 6 | 5 | 3 | 6 | 9 | 7 |
| | CMV | 1 | 2 | 3 | 2 | 22 | 2 | 4 | 3 | 3 | 3 | 3 | 10 | 2 |
| | Dog | 4 | 3 | 4 | 4 | 5 | 5 | 6 | 4 | 4 | 6 | 5 | 10 | 4 |
| | EBV | 3 | 7 | 5 | 3 | 5 | 4 | 5 | 5 | 3 | 4 | 5 | 10 | 5 |
| | Green-monkey | 8 | 2 | 3 | 8 | 8 | 9 | 9 | 7 | 7 | 9 | 9 | 12 | 7 |
| | Guinean pig | 2 | 2 | 3 | 2 | 2 | 3 | 4 | 2 | 3 | 3 | 3 | 8 | 3 |
| | HBV | 3 | 3 | 4 | 3 | 4 | 4 | 4 | 4 | 4 | 4 | 4 | 9 | 4 |
| | HEK293T | 4 | 1 | 5 | 4 | 5 | 5 | 6 | 4 | 2 | 6 | 5 | 10 | 3 |
| | HHV 1 | 1 | 2 | 3 | 2 | 3 | 3 | 4 | 4 | 2 | 3 | 3 | 9 | 3 |
| | HHV 2 | 3 | 3 | 4 | 3 | 3 | 4 | 4 | 3 | 4 | 123 | 4 | 10 | 4 |
| | HHV 6 | 1 | 2 | 3 | 2 | 3 | 2 | 4 | 3 | 3 | 3 | 3 | 9 | 4 |
| | HHV 7 | 2 | 2 | 2 | 2 | 3 | 2 | 4 | 2 | 3 | 2 | 2 | 8 | 3 |
| | HHV 8 | 2 | 2 | 3 | 3 | 3 | 2 | 5 | 3 | 3 | 3 | 3 | 9 | 3 |
| | HPV18 | 5 | 4 | 6 | 4 | 5 | 5 | 6 | 6 | 5 | 6 | 5 | 10 | 7 |
| | M. arginini/hominis | 2 | 2 | 4 | 3 | 3 | 6 | 16 | 3 | 2 | 4 | 3 | 7 | 3 |
| | M. fermentans | 1 | 2 | 3 | 74 | 2 | 2 | 4 | 2 | 2 | 3 | 3 | 9 | 2 |
| | M. orale | 4 | 3 | 5 | 3 | 4 | 4 | 4 | 5 | 4 | 27 | 4 | 10 | 5 |
| | M. synoviae | 3 | 3 | 4 | 4 | 5 | 5 | 5 | 3 | 6 | 5 | 4 | 10 | 7 |
| | M. hyorhinis | 4 | 3 | 5 | 4 | 244 | 2 | 5 | 5 | 2 | 3 | 3 | 9 | 2 |
| | M. pneumoniae | 174 | 2 | 456 | 3 | 3 | 2 | 4 | 2 | 3 | 3 | 3 | 9 | 3 |
| | Mouse | 3 | 2 | 3 | 2 | 2 | 2 | 4 | 2 | 3 | 3 | 4 | 9 | 4 |
| | Rabbit | 1 | 2 | 3 | 2 | 2 | 2 | 4 | 4 | 2 | 3 | 3 | 9 | 2 |
| | Rat | 2 | 2 | 4 | 2 | 3 | 3 | 5 | 4 | 3 | 3 | 3 | 9 | 4 |
| | SMRV | 4 | 3 | 3 | 4 | 3 | 4 | 6 | 4 | 4 | 6 | 4 | 10 | 4 |
| | Sry hum/monk | 3 | 2 | 4 | 4 | 4 | 5 | 5 | 4 | 4 | 3 | 4 | 9 | 5 |
| | SV40 Tag | 4 | 3 | 5 | 4 | 5 | 4 | 6 | 5 | 5 | 5 | 5 | 10 | 6 |
| | SV40 VP1 | 3 | 3 | 6 | 4 | 4 | 4 | 5 | 6 | 5 | 5 | 6 | 10 | 7 |
| | SV40 VP3 | 3 | 3 | 5 | 4 | 4 | 5 | 5 | 5 | 4 | 5 | 3 | 10 | 6 |
| | VZV | 1 | 2 | 2 | 2 | 2 | 2 | 4 | 3 | 3 | 3 | 3 | 9 | 3 |
| | Y-chromosome mouse | 4 | 3 | 5 | 4 | 5 | 5 | 5 | 5 | 4 | 5 | 4 | 10 | 5 |
| | Mixture | 166 | 3 | 389 | 333 | 16 | 48 | 112 | 5 | 5 | 19 | 5 | 76 | 5 |
| | Mixture | 119 | 3 | 339 | 270 | 11 | 35 | 80 | 5 | 5 | 15 | 4 | 57 | 5 |
| | H₂O control | 5 | 4 | 4 | 4 | 4 | 4 | 4 | 3 | 3 | 5 | 5 | 9 | 5 |
| | cutoff | 11 | 10 | 10 | 10 | 10 | 10 | 10 | 9 | 9 | 11 | 11 | 16 | 11 |

[a] positive reactions are indicated in bold and underlined, some lines contain more than one target as frequently cell lines were used.

The invention claimed is:

1. A method for simultaneously determining the presence or absence of one or more contaminations in a cell culture sample comprising the steps of:
   a) contacting a sample of a cell culture suspected to comprise contaminations with a composition comprising oligonucleotides of at least three different groups of oligonucleotides, said groups being selected from:
   aa) an oligonucleotide group comprising at least one pair of oligonucleotides capable of specifically amplifying polynucleotides comprised by the squirrel monkey retrovirus (SMRV), wherein said at least one pair is selected from the following pairs of oligonucleotides:
      i) a pair of oligonucleotides consisting essentially of a nucleic acid sequence as shown in SEQ ID NO:1 and SEQ ID NO:2,
      ii) a pair of oligonucleotides consisting essentially of a nucleic acid sequence as shown in SEQ ID NO:3 and SEQ ID NO:4, and
      iii) at least one pair of oligonucleotides which are capable of specifically amplifying polynucleotides which are amplified by the oligonucleotides of (i) and/or (ii),
   bb) an oligonucleotide group comprising at least one pair of oligonucleotides capable of specifically amplifying polynucleotides comprised by different *Mycoplasma* species, wherein said at least one pair is selected from the following pairs of oligonucleotides:
      i) a pair of oligonucleotides consisting essentially of a nucleic acid sequence as shown in SEQ ID NO:5 and SEQ ID NO:6,
      ii) a pair of oligonucleotides consisting essentially of a nucleic acid sequence as shown in SEQ ID NO:7 and SEQ ID NO:8, and
      iii) at least one pair of oligonucleotides which are capable of specifically amplifying polynucleotides which are amplified by the oligonucleotides of (i) and/or (ii),
   cc) an oligonucleotide group comprising at least one pair of oligonucleotides capable of specifically amplifying polynucleotides comprised by HeLa cells wherein said at least one pair is selected from the following pairs of oligonucleotides:
      i) a pair of oligonucleotides consisting essentially of a nucleic acid sequence as shown in SEQ ID NO:9 and SEQ ID NO:10, and
      ii) a pair of oligonucleotides which are capable of specifically amplifying polynucleotides which are amplified by the oligonucleotides of (i),
   dd) an oligonucleotide group comprising at least one pair of oligonucleotides capable of specifically amplifying polynucleotides comprised by adenovirus, wherein said at least one pair is selected from the following pairs of oligonucleotides:
      i) a pair of oligonucleotides consisting essentially of a nucleic acid sequence as shown in SEQ ID NO:11 and SEQ ID NO:12, and
      ii) a pair of oligonucleotides which are capable of specifically amplifying polynucleotides which are amplified by the oligonucleotides of (i),
   ee) an oligonucleotide group comprising at least one pair of oligonucleotides capable of specifically amplifying polynucleotides comprised by *A. laidwaii* wherein said at least one pair is selected the following pairs of oligonucleotides:
      i) a pair of oligonucleotides consisting essentially of a nucleic acid sequence as shown in SEQ ID NO:13 and SEQ ID NO:14, and
      ii) a pair of oligonucleotides which are capable of specifically amplifying polynucleotides which are amplified by the oligonucleotides of (i),
   ff) an oligonucleotide group comprising at least one pair of oligonucleotides capable of specifically amplifying polynucleotides for a mammalian globin, wherein said at least one pair is selected the following pairs of oligonucleotides:
      i) a pair of oligonucleotides consisting essentially of a nucleic acid sequence as shown in SEQ ID NO:15 and SEQ ID NO:16,
      ii) a pair of oligonucleotides consisting essentially of a nucleic acid sequence as shown in SEQ ID NO:17 and SEQ ID NO:18,
      iii) a pair of oligonucleotides consisting essentially of a nucleic acid sequence as shown in SEQ ID NO:19 and SEQ ID NO:20, and
      iv) at least one pair of oligonucleotides which are capable of specifically amplifying polynucleotides which are amplified by the oligonucleotides of (i), (ii) and/or (iii),
   gg) an oligonucleotide group comprising at least one pair of oligonucleotides capable of specifically amplifying polynucleotides comprised by various hepatitis B virus (HBV) strains wherein said at least one pair is selected the following pairs of oligonucleotides:
      i) a pair of oligonucleotides consisting essentially of a nucleic acid sequence as shown in SEQ ID NO:21 and SEQ ID NO:22, and
      ii) a pair of oligonucleotides which are capable of specifically amplifying polynucleotides which are amplified by the oligonucleotides of (i),
   hh) an oligonucleotide group comprising at least one pair of oligonucleotides capable of specifically amplifying polynucleotides comprised by a herpes virus wherein said at least one pair is selected from the following pairs of oligonucleotides:

i) a pair of oligonucleotides consisting essentially of a nucleic acid sequence as shown in SEQ ID NO:23 and SEQ ID NO:24,
ii) a pair of oligonucleotides consisting essentially of a nucleic acid sequence as shown in SEQ ID NO:25 and SEQ ID NO:26,
iii) a pair of oligonucleotides consisting essentially of a nucleic acid sequence as shown in SEQ ID NO:27 and SEQ ID NO:28,
iv) a pair of oligonucleotides consisting essentially of a nucleic acid sequence as shown in SEQ ID NO:29 and SEQ ID NO:30,
v) a pair of oligonucleotides consisting essentially of a nucleic acid sequence as shown in SEQ ID NO:31 and SEQ ID NO:32,
vi) a pair of oligonucleotides consisting essentially of a nucleic acid sequence as shown in SEQ ID NO:33 and SEQ ID NO:34,
vii) a pair of oligonucleotides consisting essentially of a nucleic acid sequence as shown in SEQ ID NO:35 and SEQ ID NO:36,
viii) a pair of oligonucleotides consisting essentially of a nucleic acid sequence as shown in SEQ ID NO:37 and SEQ ID NO:38, and
ix) at least one pair of oligonucleotides which are capable of specifically amplifying polynucleotides which are amplified by the oligonucleotides of (i), (ii), (iii), (iv), (v), (vi), (vii) and/or (viii), jj) an oligonucleotide group comprising at least one pair of oligonucleotides capable of specifically amplifying polynucleotides comprised by a mammalian Y chromosome wherein said at least one pair is selected from the following pairs of oligonucleotides:
i) a pair of oligonucleotides consisting essentially of a nucleic acid sequence as shown in SEQ ID NO:39 and SEQ ID NO:40,
ii) a pair of oligonucleotides consisting essentially of a nucleic acid sequence as shown in SEQ ID NO:41 and SEQ ID NO:42,
iii) a pair of oligonucleotides consisting essentially of a nucleic acid sequence as shown in SEQ ID NO:43 and SEQ ID NO:44, and
iv) at least one pair of oligonucleotides which are capable of specifically amplifying polynucleotides which are amplified by the oligonucleotides of (i), (ii) and/or (iii), and kk) an oligonucleotide group comprising at least one pair of oligonucleotides capable of specifically amplifying polynucleotides comprised by SV40 (simian virus 40), wherein said at least one pair is selected from the following pairs of oligonucleotides:
i) a pair of oligonucleotides consisting essentially of a nucleic acid sequence as shown in SEQ ID NO:45 and SEQ ID NO:46,
ii) a pair of oligonucleotides consisting essentially of a nucleic acid sequence as shown in SEQ ID NO:47 and SEQ ID NO:48,
iii) a pair of oligonucleotides consisting essentially of a nucleic acid sequence as shown in SEQ ID NO:49 and SEQ ID NO:50, and
iv) at least one pair of oligonucleotides which are capable of specifically amplifying polynucleotides comprised by are amplified by the oligonucleotides of (i), (ii) and/or (iii), and ll) an oligonucleotide group comprising at least one pair of oligonucleotides capable of specifically amplifying polynucleotides comprised by a 16S ribosomal RNA gene of a different species, wherein said at least one pair is selected from the following pairs of oligonucleotides:
i) a pair of oligonucleotides consisting essentially of a nucleic acid sequence as shown in SEQ ID NO:53 and SEQ ID NO:54,
ii) a pair of oligonucleotides consisting essentially of a nucleic acid sequence as shown in SEQ ID NO:55 and SEQ ID NO:56,
iii) a pair of oligonucleotides consisting essentially of a nucleic acid sequence as shown in SEQ ID NO:57 and SEQ ID NO:58,
iv) a pair of oligonucleotides consisting essentially of a nucleic acid sequence as shown in SEQ ID NO:59 and SEQ ID NO:60,
v) a pair of oligonucleotides consisting essentially of a nucleic acid sequence as shown in SEQ ID NO:61 and SEQ ID NO:62,
vi) a pair of oligonucleotides consisting essentially of a nucleic acid sequence as shown in SEQ ID NO:63 and SEQ ID NO:64,
vii) a pair of oligonucleotides consisting essentially of a nucleic acid sequence as shown in SEQ ID NO:65 and SEQ ID NO:66,
viii) a pair of oligonucleotides consisting essentially of a nucleic acid sequence as shown in SEQ ID NO:149 and SEQ ID NO:150,
ix) a pair of oligonucleotides consisting essentially of a nucleic acid sequence as shown in SEQ ID NO:151 and SEQ ID NO:152,
x) a pair of oligonucleotides consisting essentially of a nucleic acid sequence as shown in SEQ ID NO:153 and SEQ ID NO:154,
xi) a pair of oligonucleotides consisting essentially of a nucleic acid sequence as shown in SEQ ID NO:155 and SEQ ID NO:156, and
xii) at least one pair of oligonucleotides which are capable of specifically amplifying polynucleotides which are amplified by the oligonucleotides of (i), (ii), (iii), (iv), (v), (vi), (vii), (viii), (ix), (x) and/or (xi); and b) simultaneously determining the contaminations in said sample based on the amplified polynucleotides obtained in step a).

2. The method of claim 1, wherein at least nine pairs of oligonucleotides of at least three different groups are selected from:
aa) an oligonucleotide group comprising at least one pair of oligonucleotides capable of specifically amplifying polynucleotides comprised by the squirrel monkey retrovirus (SMRV), wherein said at least one pair is selected from the following pairs of oligonucleotides:
i) a pair of oligonucleotides consisting essentially of a nucleic acid sequence as shown in SEQ ID NO:1 and SEQ ID NO:2, and
ii) a pair of oligonucleotides consisting essentially of a nucleic acid sequence as shown in SEQ ID NO:3 and SEQ ID NO:4, bb) an oligonucleotide group comprising at least one pair of oligonucleotides capable of specifically amplifying polynucleotides comprised by different *Mycoplasma* species, wherein said at least one pair is selected from the following pairs of oligonucleotides:
i) a pair of oligonucleotides consisting essentially of a nucleic acid sequence as shown in SEQ ID NO:5 and SEQ ID NO:6, and ii) a pair of oligonucleotides consisting essentially of a nucleic acid sequence as shown in SEQ ID NO:7 and SEQ ID NO:8,
cc) a pair of oligonucleotides consisting essentially of a nucleic acid sequence as shown in SEQ ID NO:9 and SEQ ID NO:10,
dd) a pair of oligonucleotides consisting essentially of a nucleic acid sequence as shown in SEQ ID NO:11 and SEQ ID NO:12,
ee) a pair of oligonucleotides consisting essentially of a nucleic acid sequence as shown in SEQ ID NO:13 and SEQ ID NO:14,
ff) an oligonucleotide group comprising at least one pair of oligonucleotides capable of specifically amplifying polynucleotides for a mammalian globin, wherein said at least one pair is selected the following pairs of oligonucleotides:
  i) a pair of oligonucleotides consisting essentially of a nucleic acid sequence as shown in SEQ ID NO:15 and SEQ ID NO:16,
  ii) a pair of oligonucleotides consisting essentially of a nucleic acid sequence as shown in SEQ ID NO:17 and SEQ ID NO:18, and
  iii) a pair of oligonucleotides consisting essentially of a nucleic acid sequence as shown in SEQ ID NO:19 and SEQ ID NO:20,
gg) a pair of oligonucleotides consisting essentially of a nucleic acid sequence as shown in SEQ ID NO:21 and SEQ ID NO:22,
hh) an oligonucleotide group comprising at least one pair of oligonucleotides capable of specifically amplifying polynucleotides comprised by a herpes virus wherein said at least one pair is selected from the following pairs of oligonucleotides:
  i) a pair of oligonucleotides consisting essentially of a nucleic acid sequence as shown in SEQ ID NO:23 and SEQ ID NO:24,
  ii) a pair of oligonucleotides consisting essentially of a nucleic acid sequence as shown in SEQ ID NO:25 and SEQ ID NO:26,
  iii) a pair of oligonucleotides consisting essentially of a nucleic acid sequence as shown in SEQ ID NO:27 and SEQ ID NO:28,
  iv) a pair of oligonucleotides consisting essentially of a nucleic acid sequence as shown in SEQ ID NO:29 and SEQ ID NO:30,
  v) a pair of oligonucleotides consisting essentially of a nucleic acid sequence as shown in SEQ ID NO:31 and SEQ ID NO:32,
  vi) a pair of oligonucleotides consisting essentially of a nucleic acid sequence as shown in SEQ ID NO:33 and SEQ ID NO:34,
  vii) a pair of oligonucleotides consisting essentially of a nucleic acid sequence as shown in SEQ ID NO:35 and SEQ ID NO:36, and
  viii) a pair of oligonucleotides consisting essentially of a nucleic acid sequence as shown in SEQ ID NO:37 and SEQ ID NO:38,
jj) an oligonucleotide group comprising at least one pair of oligonucleotides capable of specifically amplifying polynucleotides comprised by a mammalian Y chromosome wherein said at least one pair is selected from the following pairs of oligonucleotides:
  i) a pair of oligonucleotides consisting essentially of a nucleic acid sequence as shown in SEQ ID NO:39 and SEQ ID NO:40,
  ii) a pair of oligonucleotides consisting essentially of a nucleic acid sequence as shown in SEQ ID NO:41 and SEQ ID NO:42, and
  iii) a pair of oligonucleotides consisting essentially of a nucleic acid sequence as shown in SEQ ID NO:43 and SEQ ID NO:44,
kk) an oligonucleotide group comprising at least one pair of oligonucleotides capable of specifically amplifying polynucleotides comprised by SV40 (simian virus 40), wherein said at least one pair is selected from the following pairs of oligonucleotides:
  i) a pair of oligonucleotides consisting essentially of a nucleic acid sequence as shown in SEQ ID NO:45 and SEQ ID NO:46,
  ii) a pair of oligonucleotides consisting essentially of a nucleic acid sequence as shown in SEQ ID NO:47 and SEQ ID NO:48, and
  iii) a pair of oligonucleotides consisting essentially of a nucleic acid sequence as shown in SEQ ID NO:49 and SEQ ID NO:50.

3. The method of claim 1, wherein in step a) the oligonucleotide mixture further comprises oligonucleotides capable of amplifying a fragment of the polymerase A (PolA) polynucleotide, wherein said oligonucleotides bind to highly conserved regions of the PolA-polynucleotide.

4. The method of claim 3, wherein the oligonucleotides capable of amplifying a fragment of the polymerase A (PolA) polynucleotide have a nucleic acid sequence as shown in SEQ ID NO:51 and SEQ ID NO:52.

5. The method of claim 1, wherein the amplified polynucleotides are obtained by polymerase chain reaction.

6. The method of claim 1, wherein the determination of the various amplified polynucleotides comprises the step of hybridizing the amplified polynucleotides with probe oligonucleotides that specifically bind to the amplified polynucleotides.

7. The method of claim 6, wherein the probe oligonucleotides that specifically bind to the amplified polynucleotides are selected from the group consisting of probe oligonucleotides comprising a nucleic acid sequence as shown in SEQ ID No. 78 to 119, and SEQ ID No. 121 to 134, and SEQ ID No. 145 to 148.

* * * * *